United States Patent
Gurney et al.

(10) Patent No.: US 11,104,660 B2
(45) Date of Patent: Aug. 31, 2021

(54) PDE4D INHIBITORS

(71) Applicant: TETRA DISCOVERY PARTNERS, INC., Grand Rapids, MI (US)

(72) Inventors: Mark E. Gurney, Grand Rapids, MI (US); Xuesheng Mo, Naperville, IL (US); Richard Allen Nugent, Kalamazoo, MI (US); Donna Lee Romero, Chesterfield, MO (US)

(73) Assignee: TETRA DISCOVERY PARTNERS, INC., Grand Rapids, MI (US)

( * ) Notice: Subject to any disclaimer, the term of this patent is extended or adjusted under 35 U.S.C. 154(b) by 0 days.

(21) Appl. No.: 16/856,122

(22) Filed: Apr. 23, 2020

(65) Prior Publication Data

US 2020/0339532 A1  Oct. 29, 2020

Related U.S. Application Data

(60) Provisional application No. 62/837,297, filed on Apr. 23, 2019.

(51) Int. Cl.
*C07D 401/06* (2006.01)
*C07D 239/42* (2006.01)

(52) U.S. Cl.
CPC ......... *C07D 401/06* (2013.01); *C07D 239/42* (2013.01)

(58) Field of Classification Search
CPC ........................... C07D 401/06; C07D 239/42
See application file for complete search history.

(56) References Cited

U.S. PATENT DOCUMENTS 9,120,770 B2 * 9/2015 Bollu .................. C07D 239/34

FOREIGN PATENT DOCUMENTS

WO  WO-2009/067600 A2  5/2009
WO  WO-2014/158998 A1  10/2014

OTHER PUBLICATIONS

Barad et al., Rolipram, a Type IV-specific Phosphodiesterase Inhibitor, Facilitates the Establishment of Long-Lasting Long-Term Potentiation and Improves Memory, Proc. Natl. Acad. Sci. USA, 95(25):15020-5 (1998).
Frey et al., Effects of cAMP Simulate a Late Stage of LTP in Hippocampal CA1 Neurons, Science, 260(5114):1661-4 (1993).
Fujita et al., Downregulation of Brain Phosphodiesterase Type IV Measured With 11C-(R)-rolipram Positron Emission Tomography in Major Depressive Disorder, Biol. Psychiatry, 72(7):548-54 (2012).
International Application No. PCT/US2020/029427, International Search Report and Written Opinion, dated Jul. 10, 2020.
Rose et al., Phosphodiesterase Inhibitors for Cognitive Enhancement, Curr. Pharm. Des., 11(26):3329-34 (2005).
Wakabayashi et al., Discovery, Radiolabeling, and Evaluation of Subtype-Selective Inhibitors for Positron Emission Tomography Imaging of Brain Phosphodiesterase-4D, ACS Chem Neurosci., 11(9):1311-23 (2020).

* cited by examiner

*Primary Examiner* — Erich A Leeser
(74) *Attorney, Agent, or Firm* — Marshall, Gerstein & Borun LLP

(57) ABSTRACT

Provided herein are phosphodiesterase 4D (PDE4D) inhibitors, including methods of using the same. Also provided are methods of treating subjects suffering from conditions associated with aberrant PDE activity.

22 Claims, No Drawings

PDE4D INHIBITORS

STATEMENT OF GOVERNMENT INTEREST

This invention was made with government support under MH107077 awarded by the National Institutes of Health. The government has certain rights in the invention.

BACKGROUND

It is known that cAMP-specific phosphodiesterase-4 (PDE4) is an enzyme related to second messenger cAMP regulation and deeply related to learning and memory functions (Science 1993, 260: 1661-4). It has been shown that PDE4 inhibitors promote neuronal plasticity in vitro, and improve or promote learning and memory in various models in vivo (PNAS 1998, 95: 15020-5; Current Pharmaceutical Design 2005, 11: 3329-34). Further, PDE4 enzyme levels are decreased in major depression and a decrease in cAMP signal transduction in a pathological condition can be assumed (Biological Psychiatry 2012, 72548-54). PDE4D is one isoform of PDE4 and has been implicated in the etiology in a host of different diseases.

There is a need for PDE4D inhibitors.

SUMMARY

Provided herein are compounds having a structure of Formula (I), or a pharmaceutically acceptable salt thereof:

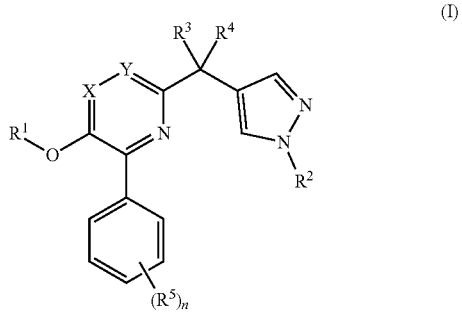

(I)

wherein, $R^1$ is H, $C_{1-6}$ alkyl, or $C_{1-6}$ haloalkyl; $R^2$ is H, $C_{1-3}$ alkyl, or $C_{1-3}$ haloalkyl; $R^3$ and $R^4$ are each H or D, and at least one of $R^3$ and $R^4$ is D; each $R^5$ is independently halo, CN, OH, $NO_2$, $C_{1-6}$ alkoxy, $C_{1-6}$ haloalkoxy, $C_{1-6}$ alkyl, $C_{1-6}$ haloalkyl, O—$C_{3-6}$cycloalkyl, $C_{1-6}$ hydroxyalkyl, or —$SO_2C_{1-3}$ alkyl; X and Y are each independently $CR^6$ or N; each $R^6$ is independently H, $C_{1-3}$ alkyl, or $C_{1-3}$ haloalkyl, and n is 0, 1, 2, 3, or 4. Also provided herein are compositions comprising the compound having a structure of Formula (I) and a pharmaceutically acceptable excipient.

The disclosure further provides methods comprising administering to a subject a compound having a structure of Formula (I) and subjecting the subject to an imaging modality.

Further provided are methods of treating a subject suffering from a condition associated with aberrant PDE activity comprising administering to the subject a therapeutically effective amount of a compound having the structure of Formula (I), with the proviso that the compound does not comprise $^{11}C$ or $^{18}F$.

Further aspects and advantages will be apparent to those of ordinary skill in the art from a review of the following detailed description. The description hereafter includes specific embodiments with the understanding that the disclosure is illustrative, and is not intended to limit the disclosure to the specific embodiments described herein.

DETAILED DESCRIPTION

Disclosed herein are compounds of Formula (I), and methods of using the same, e.g., to inhibit PDE4D. The compounds described herein have a structure of Formula (I):

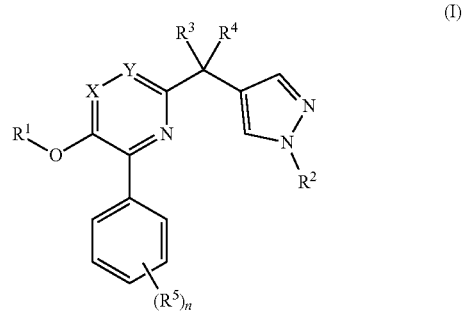

(I)

wherein the substituents are described in detail below.

Chemical Definitions

As used herein, the term "alkyl" refers to straight chained and branched saturated hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term $C_n$ means the alkyl group has "n" carbon atoms. For example, $C_4$ alkyl refers to an alkyl group that has 4 carbon atoms. The term $C_{m-n}$ means the alkyl group has "m" to "n" carbon atoms. For example, $C_{1-6}$ alkyl refers to an alkyl group having a number of carbon atoms encompassing the entire range (i.e., 1 to 6 carbon atoms), as well as all sub groups (e.g., 1-5, 1-4, 2-6, 2-5, 3-6, 3-5, 1, 2, 3, 4, 5, and 6 carbon atoms). Unless otherwise indicated, an alkyl group can be an unsubstituted alkyl group or a substituted alkyl group. For example, an alkyl (e.g., methyl) group can be substituted with one or more, and typically one to three, of independently selected halo, hydroxy, alkoxy, nitro, cyano, alkylamino, or amino groups.

Specific substitutions on an alkyl group can be indicated by inclusion in the alkyl term, e.g., "haloalkyl" or "hydroxyalkyl" which mean an alkyl group substituted with at least one halo or one hydroxyl, respectively. A haloalkyl group can be perhalogenated. Alkyl groups can be substituted with more than one type of substitution.

The term "alkoxy" is defined as —OR, wherein R is alkyl.

The term "cycloalkyl" refers to an aliphatic cyclic hydrocarbon group. The term $C_n$ means the cycloalkyl group has "n" carbon atoms. For example, $C_5$ cycloalkyl refers to a cycloalkyl group that has 5 carbon atoms in the ring. $C_{3-6}$ cycloalkyl refers to cycloalkyl groups having a number of carbon atoms encompassing the entire range (i.e., 3 to 6 carbon atoms), as well as all subgroups (e.g., 3-5, 3-4, 4-6, 4-5, 3, 4, 5, or 6 carbon atoms). Nonlimiting examples of cycloalkyl groups include cyclopropyl, cyclobutyl, cyclopentyl, and cyclohexyl. Unless otherwise indicated, a cycloalkyl group can be an unsubstituted cycloalkyl group or a substituted cycloalkyl group.

The compounds disclosed herein include isotopically-labeled compounds wherein one or more atoms of the compounds disclosed herein are replaced by atoms having the same atomic number, but an atomic mass or mass number different from the atomic mass or mass number usually found in nature, examples of which include isotopes of hydrogen, such as $^2$H and $^3$H, isotopes of carbon, such as $^{11}$C and $^{13}$C, and isotopes of fluorine, such as $^{18}$F. In some cases, one or more hydrogen atoms of the compounds disclosed herein are specifically $^2$H ("D" or deuterium). In some cases, one or more carbon atoms of the compounds disclosed herein are specifically $^{11}$C. In some cases, one or more fluorine atoms of the compounds disclosed herein are specifically $^{18}$F. In some cases, the isotopically labeled compound can be used for diagnostic or imaging purposes. In some cases, the isotopically labeled compound can be used as the therapeutic, and in such cases, may not include a $^{11}$C or $^{18}$F. Isotopically-labeled compounds as disclosed herein can be prepared by techniques known to those skilled in the art or by processes analogous to those described in the accompanying examples and schemes using an appropriate isotopically-labeled reagent in place of the non-labeled reagent previously employed.

Certain compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Compounds of the Disclosure

Provided herein are compounds having a structure of Formula (I), wherein

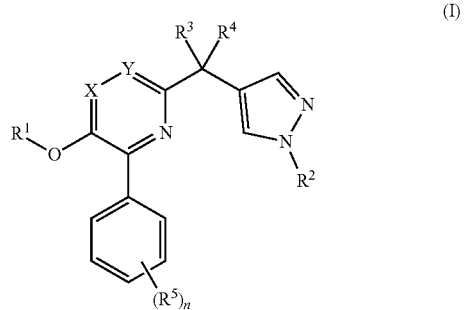

(I)

$R^1$ is H, $C_{1-6}$ alkyl, or $C_{1-6}$ haloalkyl; $R^2$ is H, $C_{1-3}$ alkyl, or $C_{1-3}$ haloalkyl; $R^3$ and $R^4$ are each H or D, and at least one of $R^3$ and $R^4$ is D; each $R^5$ is independently halo, CN, OH, NO$_2$, $C_{1-6}$ alkoxy, $C_{1-6}$ haloalkoxy, $C_{1-6}$ alkyl, $C_{1-6}$ haloalkyl, O—$C_{3-6}$ cycloalkyl, $C_{1-6}$ hydroxyalkyl, or SO$_2$C$_{1-3}$ alkyl; X and Y are each independently CR$^6$ or N, each R$^6$ is independently H, $C_{1-3}$ alkyl, or $C_{1-3}$ haloalkyl; and n is 0, 1, 2, 3, or 4.

As disclosed herein, $R^1$ is H, $C_{1-6}$ alkyl, or $C_{1-6}$ haloalkyl. Accordingly, in some embodiments, $R^1$ is H. In some embodiments, $R^1$ is $C_{1-6}$ alkyl. For example, in some cases, $R^1$ can be methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, or 2-ethylbutyl. In some embodiments, $R^1$ is methyl. In some embodiments, $R^1$ is $C_{1-6}$ alkyl and at least one carbon of the $C_{1-6}$ alkyl is $^{11}$C. For example, $R^1$ can be methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, or 2-ethylbutyl, wherein any one or more of the carbon atoms is $^{11}$C. In some cases, $R^1$ is $^{11}$CH$_3$. In some embodiments, $R^1$ is $C_{1-6}$ haloalkyl. For example, in some cases, $R^1$ is CH$_2$F. In some cases, $R^1$ is CHF$_2$. In some embodiments, the haloalkyl comprises at least one isotope having an atomic mass or mass number different from the atomic mass or mass number usually found in nature, such as $^{18}$F. For example, in some cases, $R^1$ is CH$_2{}^{18}$F. In some cases, $R^1$ is CHF$^{18}$F or CH($^{18}$F)$_2$.

As disclosed herein, $R^2$ is H, $C_{1-3}$ alkyl, or $C_{1-3}$ haloalkyl. Accordingly, in some embodiments, $R^2$ is H. In some embodiments, $R^2$ is $C_{1-3}$ alkyl. For example, in some cases, $R^2$ can be methyl, ethyl, n-propyl, or i-propyl. In some cases, $R^2$ is CH$_3$. In some embodiments, $R^2$ is $C_{1-3}$ alkyl and at least one carbon of the $C_{1-3}$ alkyl is $^{11}$C. For example, $R^2$ can be methyl, ethyl, n-propyl, or i-propyl, where in any one or more of the carbon atoms is $^{11}$C. In some cases, $R^2$ is $^{11}$CH$_3$. In some embodiments, $R^2$ is $C_{1-3}$ haloalkyl. For example, in some cases $R^2$ is CH$_2$F. In some cases, $R^2$ is CHF$_2$. In some embodiments, the haloalkyl comprises at least one isotope having an atomic mass or mass number different from the atomic mass or mass number usually found in nature, such as $^{18}$F. For example, in some cases, $R^2$ is CH$_2{}^{18}$F. In some cases, $R^2$ is CHF$^{18}$F or CH($^{18}$F)$_2$.

As disclosed herein, $R^3$ and $R^4$ are each H or D, and at least one of $R^3$ and $R^4$ is D. In some embodiments, each of $R^3$ and $R^4$ is D. In some embodiments, one of $R^3$ and $R^4$ is D and the other is H, for example, in some cases $R^3$ is H and $R^4$ is D, or $R^3$ is D and $R^4$ is H. Surprisingly and advantageously, it was found that when a compound that includes at least one deuterium atom at the $R^3$ or $R^4$ position is used in positron emission tomography (PET), the resulting image has a significantly improved signal-to-noise ratio than when there are only hydrogen atoms at this position. Without intending to be bound by theory, it is believed that by positioning deuterium atom(s) on the methylene linker, the compound cannot metabolize at this position, leading to an improved signal-to-noise ratio as compared to a compound have a hydrogenated methylene linker.

As disclosed herein, each $R^5$ is independently halo, CN, OH, NO$_2$, $C_{1-6}$alkoxy, $C_{1-6}$ haloalkoxy, $C_{1-6}$ alkyl, $C_{1-6}$ haloalkyl, O—$C_{3-6}$ cycloalkyl, $C_{1-6}$ hydroxyalkyl, or SO$_2$C$_{1-3}$ alkyl. The compounds as disclosed herein can include any number of $R^5$ groups in a range of 0 to 4. For example, the compound may include 0, 1, 2, 3, or 4R$^5$ groups. In some embodiments, n is 1. In some embodiments, n is 2. In some embodiments, n is 3. In some embodiments, n is 4. In some cases, at least one $R^5$ is NO$_2$. In some cases, at least one $R^5$ is halo. For example, in some cases, at least one $R^5$ is F, Cl, I, or Br. For example, in some aspects, at least one $R^5$ is Cl. In some aspects, at least one $R^5$ is F. In some cases wherein at least one $R^5$ is F, F is $^{18}$F. In some cases, at least one $R^5$ is CN. In some cases, at least one $R^5$ is OH. In some cases, at least one $R^5$ is $C_{1-6}$ alkoxy. In some cases, at least one $R^5$ is $C_{1-6}$ haloalkoxy. In some cases, at least one $R^5$ is $C_{1-6}$ alkyl. In some cases, at least one $R^5$ is $C_{1-6}$ haloalkyl. In some cases, at least one $R^5$ is O—$C_{3-6}$ cycloalkyl. In some cases, at least one $R^5$ is $C_{1-6}$ hydroxyalkyl. In some cases, at least one $R^5$ is $SO_2C_{1-3}$ alkyl. In some cases wherein n is 2, one $R^5$ is halo and the other is $NO_2$. For example, one $R^5$ can be F and the other can be $NO_2$. In cases wherein one $R^5$ is F and the other is $NO_2$, F can be $^{18}F$.

As disclosed herein, X and Y are each independently $CR^6$ or N. Each $R^6$ is independently H, $C_{1-3}$ alkyl, or $C_{1-3}$ haloalkyl. In some embodiments, X is CH. In some embodiments, X is N. In some embodiments, X is $CR^6$ and $R^6$ is $C_{1-3}$ alkyl, such as, for example, methyl, ethyl, n-propyl, or i-propyl. In some embodiments, X is $CR^6$ and $R^6$ is $C_{1-3}$ haloalkyl, such as, for example, trifluoromethyl, difluoromethyl, fluoromethyl, or perfluoroethyl. In some embodiments, Y is CH. In some embodiments Y is N. In some embodiments, Y is $CR^6$ and $R^6$ is $C_{1-3}$ alkyl, such as, for example, methyl, ethyl, n-propyl, or i-propyl. In some embodiments, Y is $CR^6$ and $R^6$ is $C_{1-3}$ haloalkyl, such as, for example, trifluoromethyl, difluoromethyl, fluoromethyl, or perfluoroethyl. In some embodiments, both of X and Y are $CR^6$. In some cases, both of X and Y are CH. In some embodiments, both of X and Y are N. In some embodiments X is N and Y is $CR^6$. In some embodiments, X is $CR^6$ and Y is N.

In some embodiments of the disclosure, the compound has a structure:

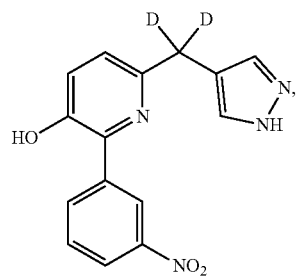

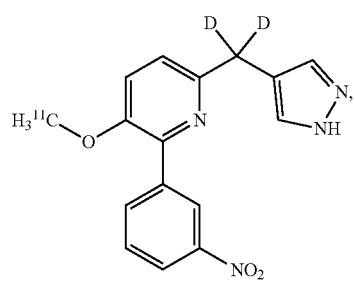

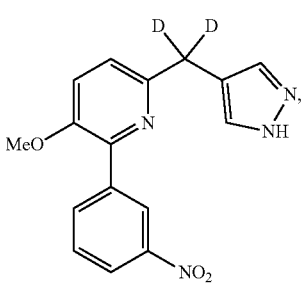

-continued

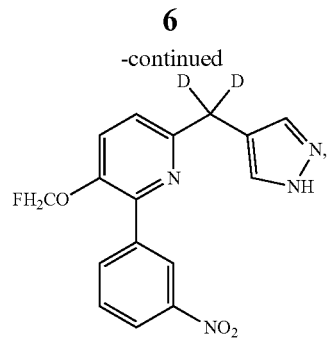

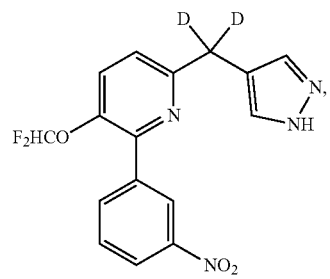

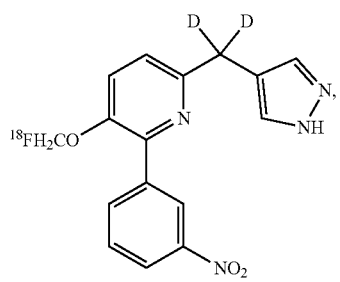

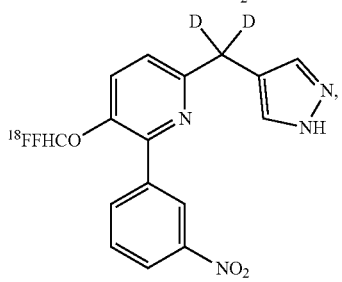

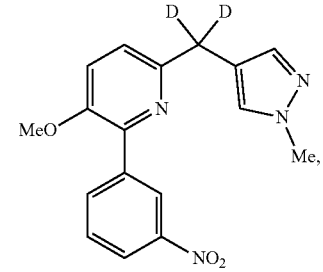

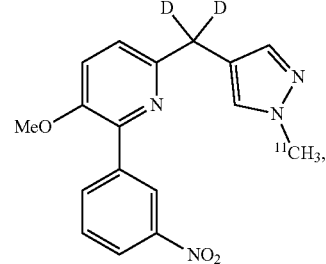

-continued

-continued
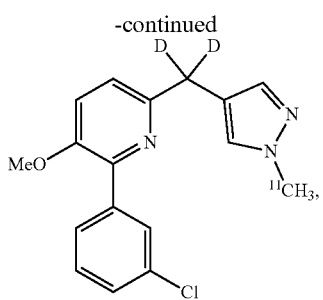
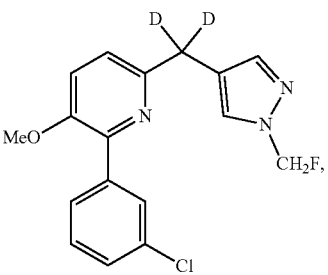
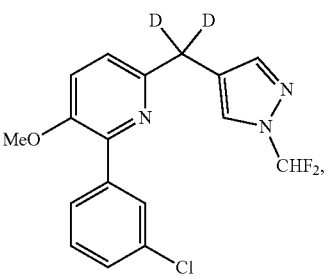
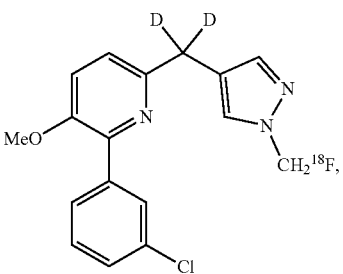
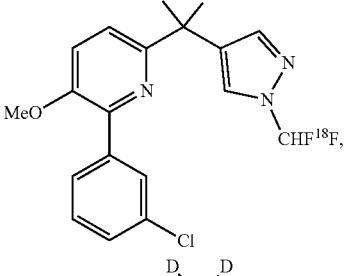
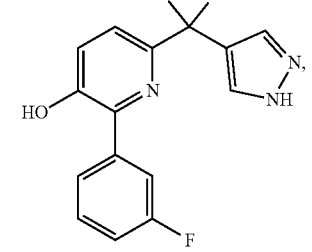
-continued
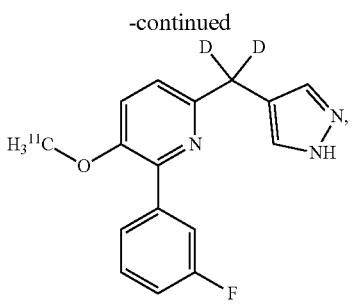
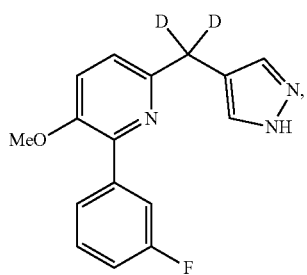
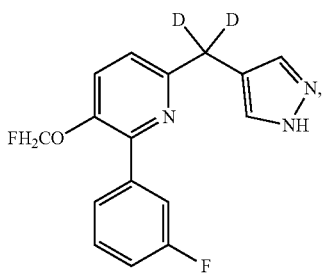
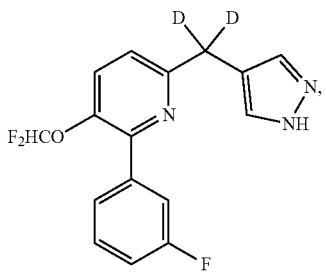
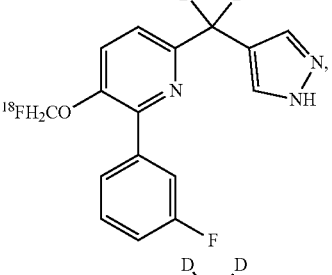
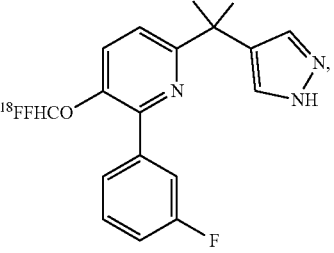

-continued
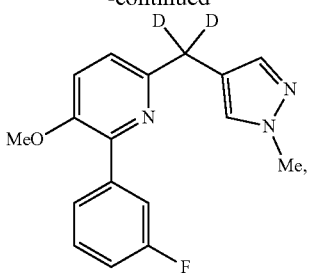
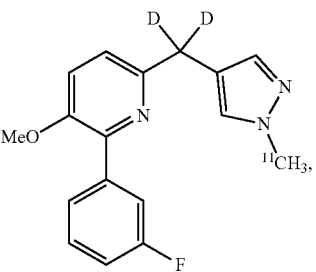
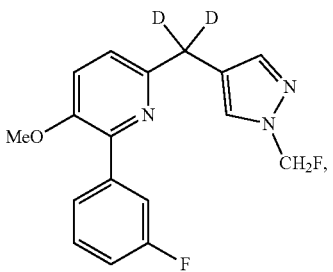
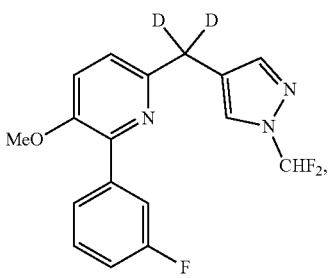
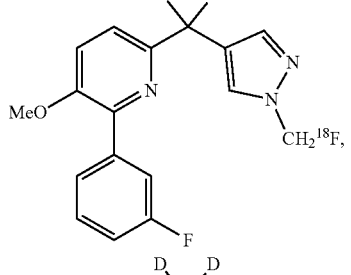
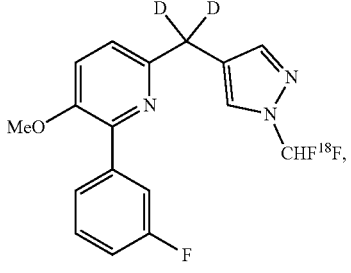
-continued
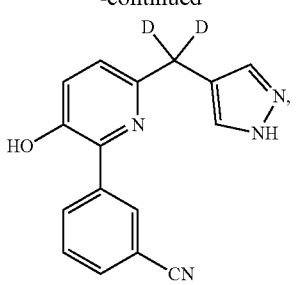
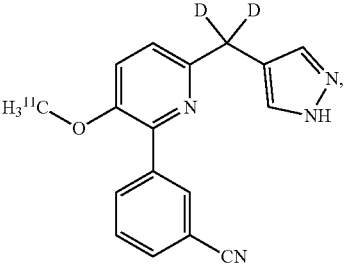
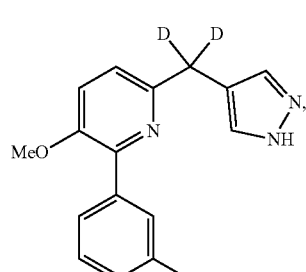
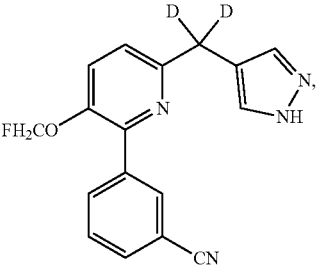
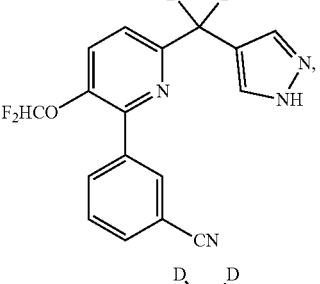
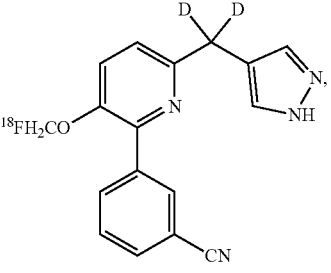

-continued
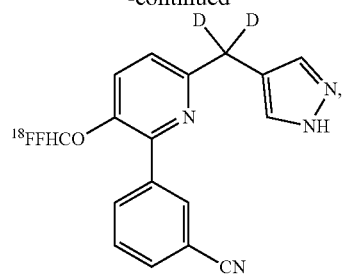
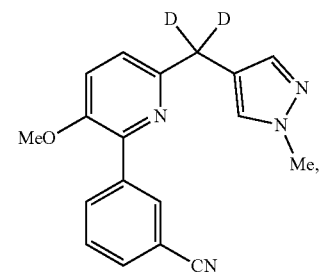
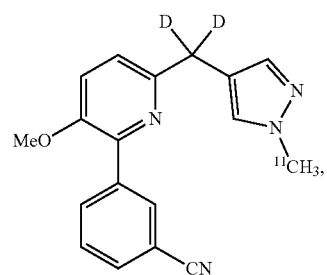
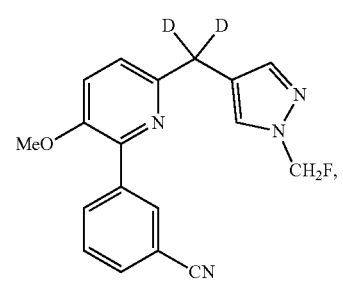
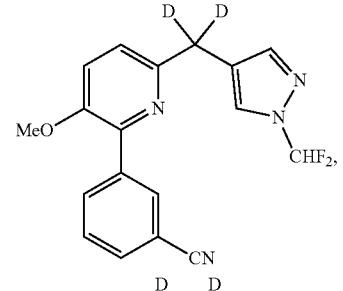
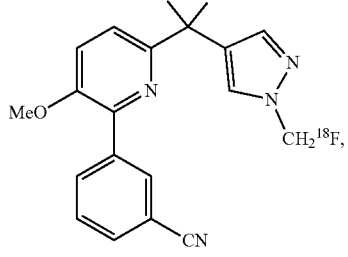
-continued
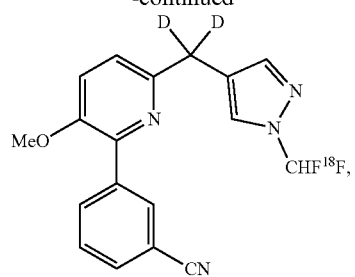
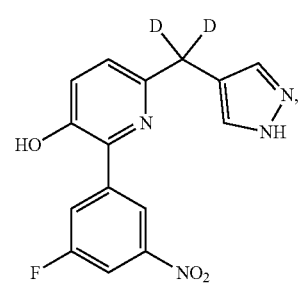
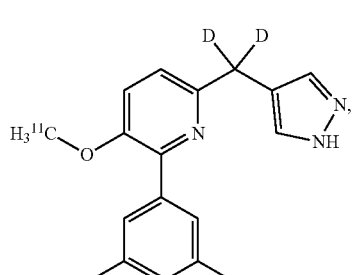
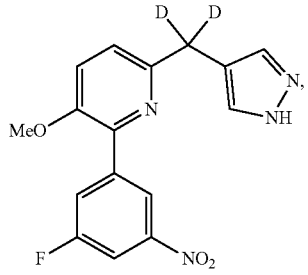
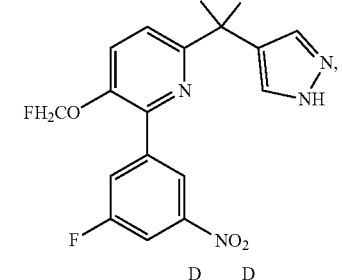
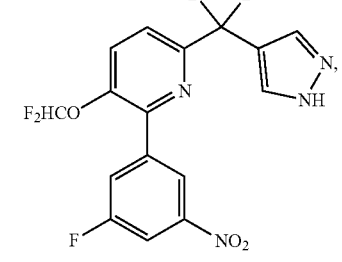

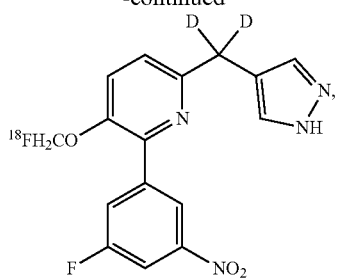
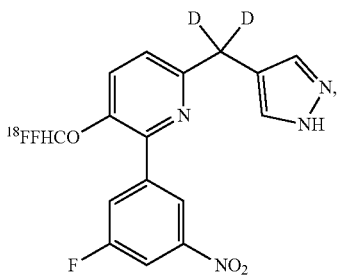
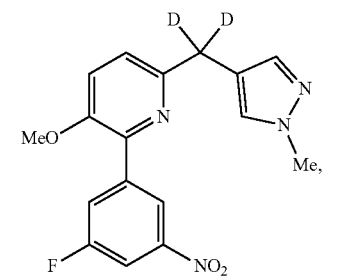
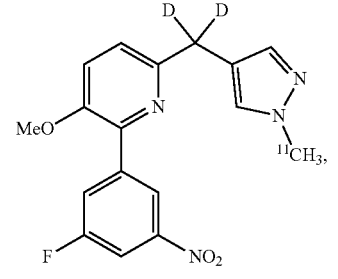
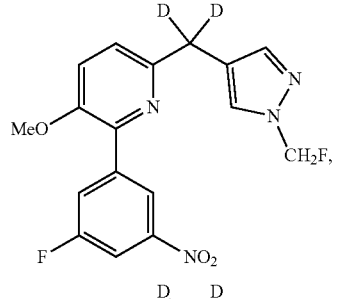
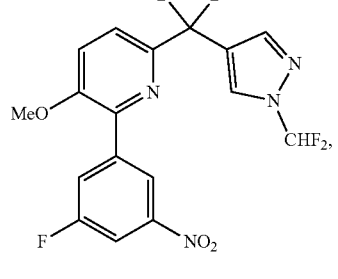
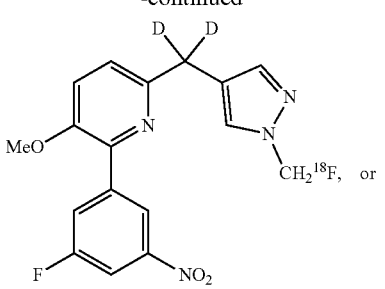
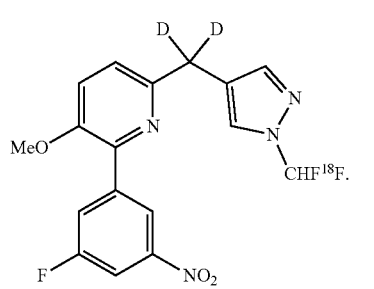
In some embodiments, the compound has a structure:
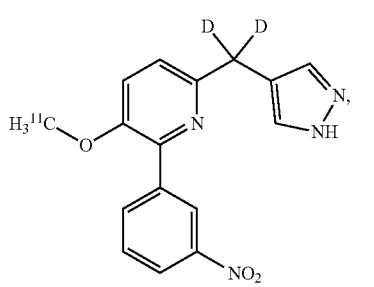
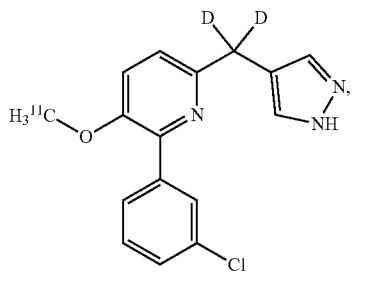
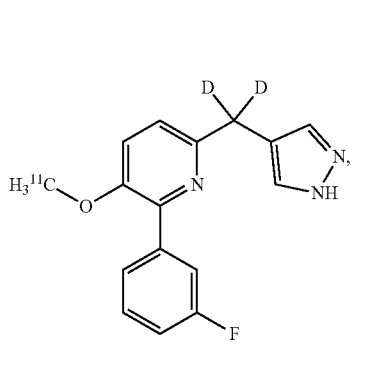

-continued
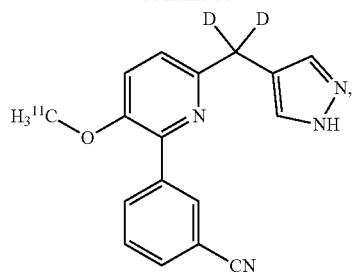
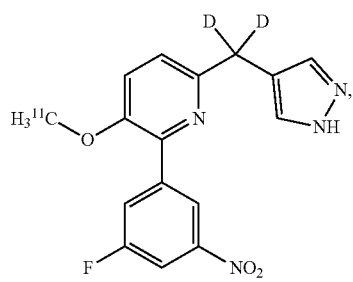
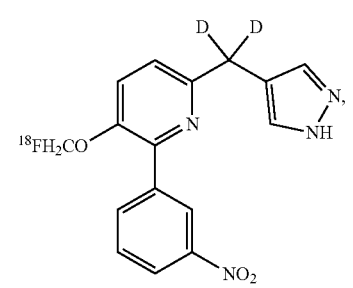
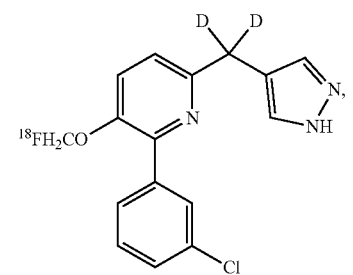
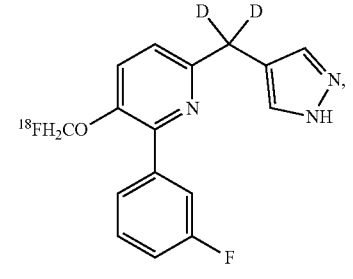
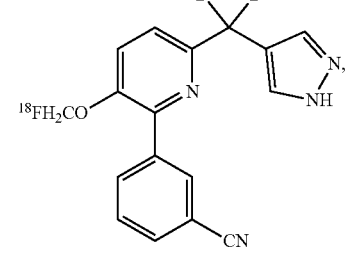
-continued
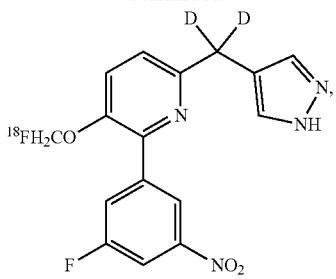
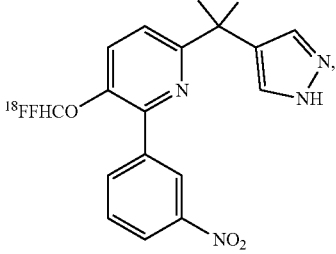
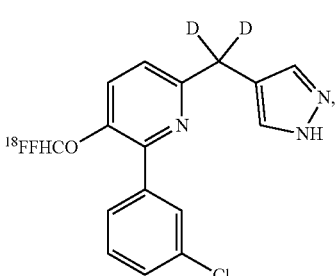
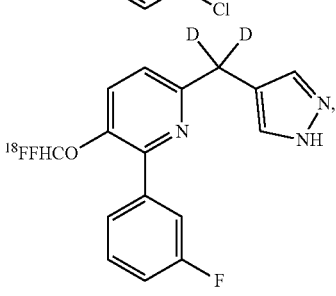
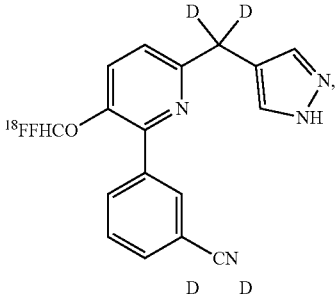
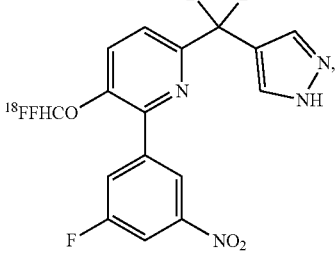

-continued
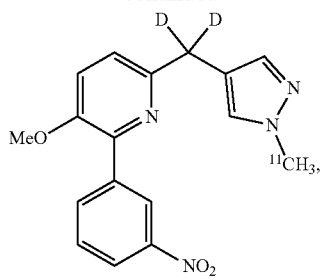
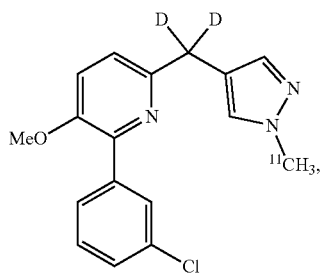
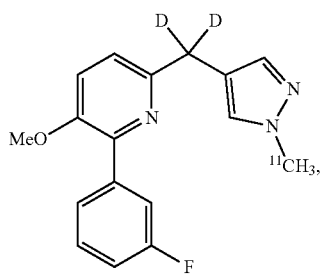
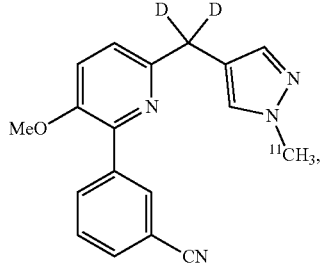
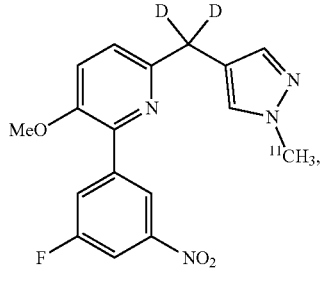
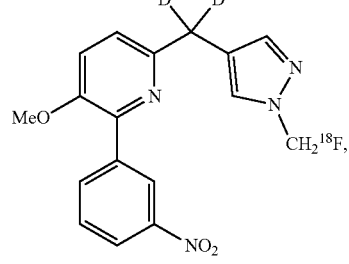
-continued
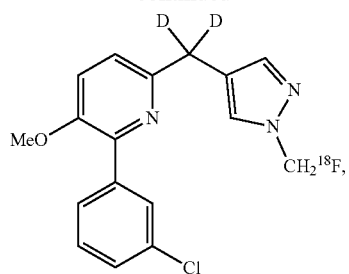
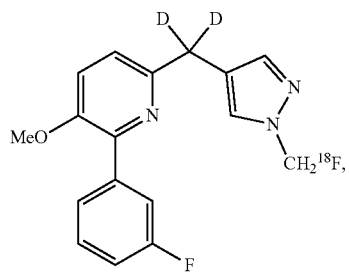
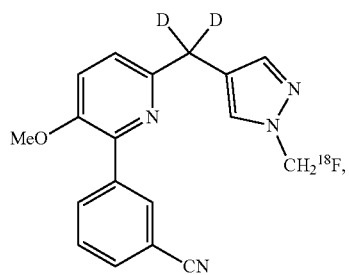
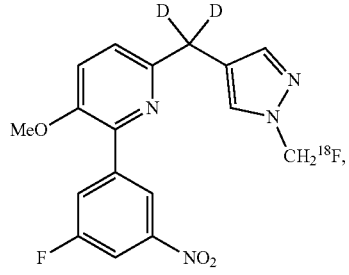
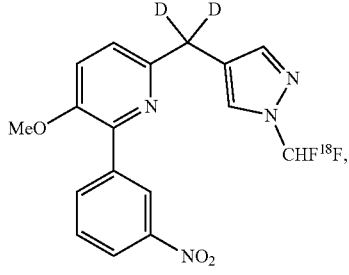
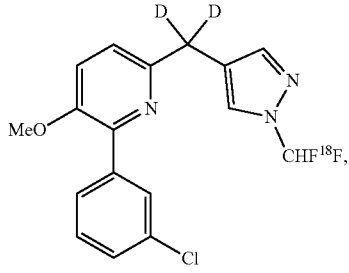

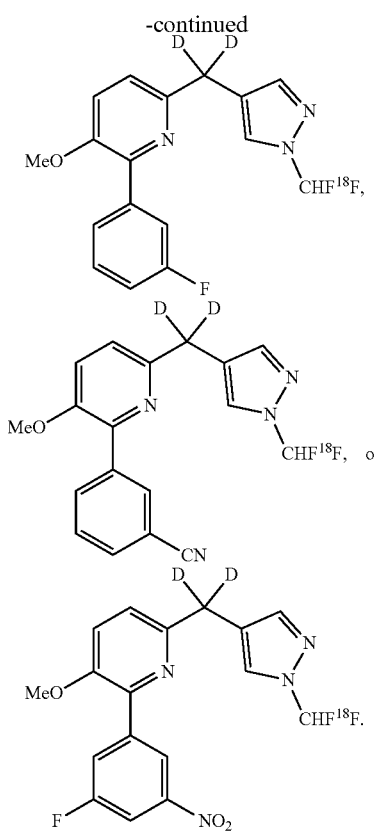

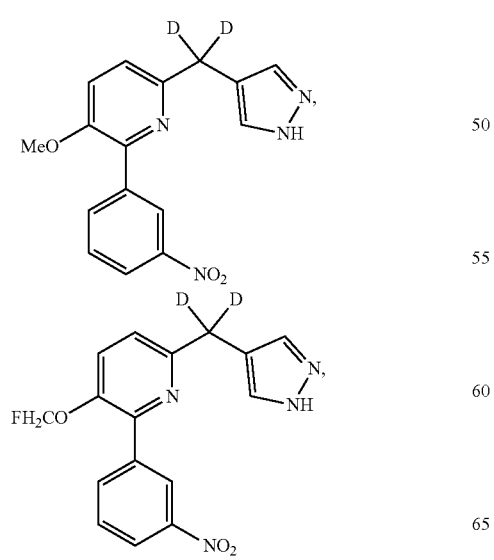

It will be appreciated by the person of ordinary skill in the art that compounds according to the disclosure which comprise an isotope such as $^{11}$C or $^{18}$F could be useful for imaging. For example, compounds which comprise an isotope such as $^{11}$C or $^{18}$F could be useful for imaging modalities including, but not limited to, positron emission tomography (PET), positron emission tomography/computed tomography (PET/CT), positron emission tomography/magnetic resonance imaging (PET/MRI), and single-photon emission computerized tomography (SPECT).

In embodiments, the compound has a structure:

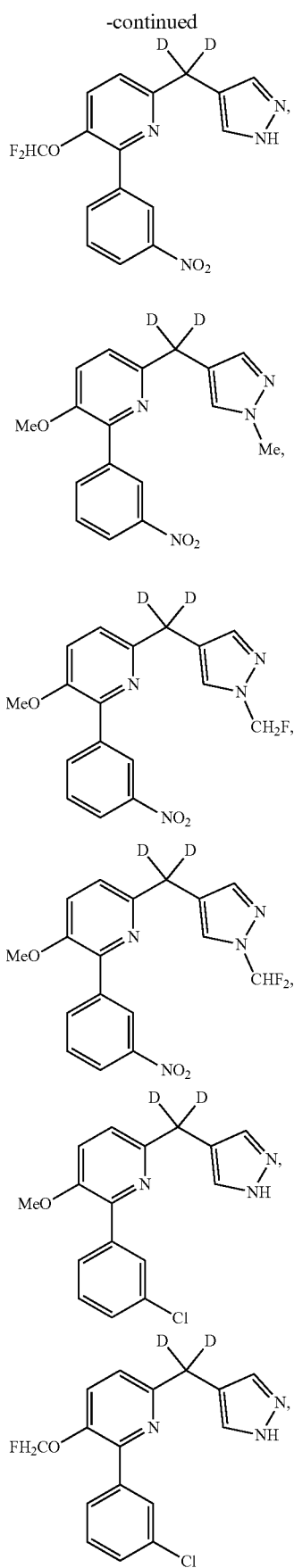

-continued
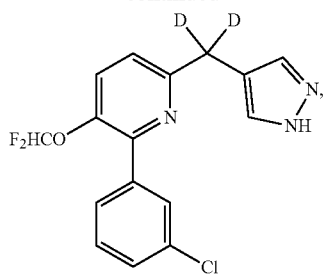
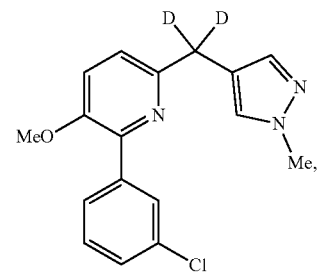
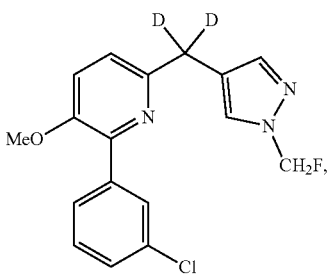
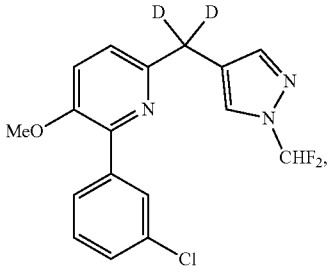
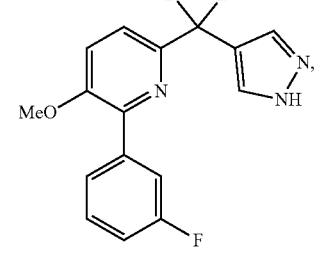
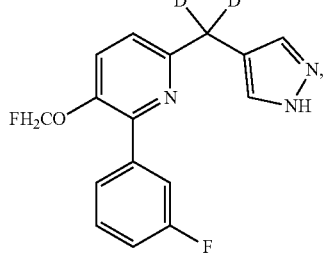
-continued
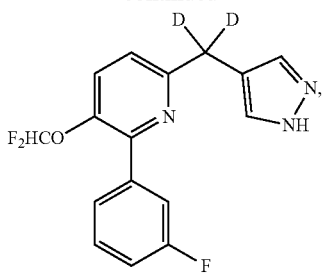
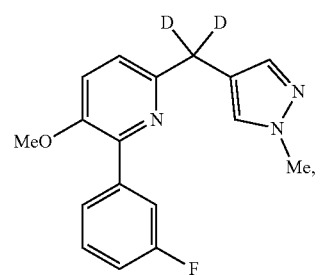
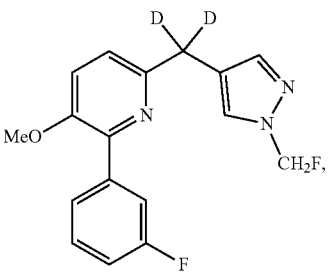
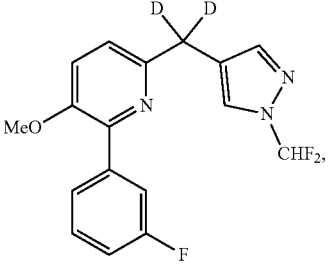
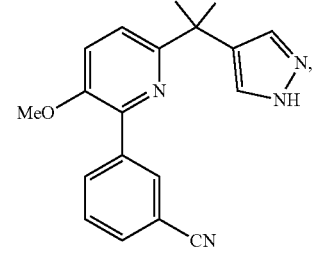
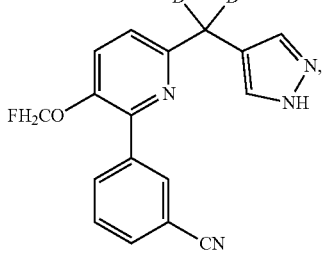

-continued

In some embodiments, the compound has a structure:

-continued

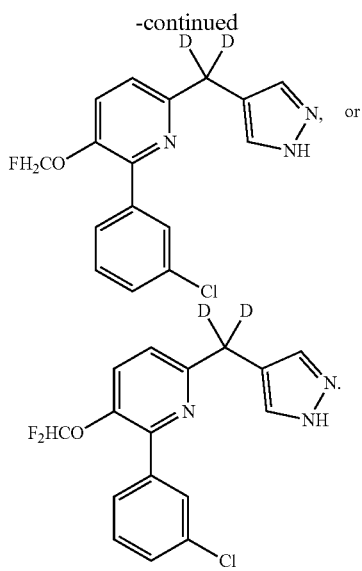

Compounds according to the disclosure that do not include an isotopic-label such as $^{11}C$ or $^{18}F$ can be suitable for use in treating PDE aberrant disorders, as described in more detail, below.

In embodiments, the compounds according to the disclosure can be in the form of a salt.

Compositions, Routes of Administration, and Dosing of PDE4D Inhibitors

Also provided herein are compositions that includes a compound as disclosed herein, together with a pharmaceutically acceptable excipient, such as a diluent or carrier. Compounds and pharmaceutical compositions suitable for use according to the disclosure include those wherein the compound can be administered in an effective amount to achieve its intended purpose. Administration of the compound described in more detail below.

Suitable pharmaceutical formulations can be determined by the person of ordinary skill in the art depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

Dosages of the therapeutic can be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. The therapeutic can be administered once a day, twice a day, three times a day, every other day, twice a week, once a week, once every two weeks or once a month. While individual needs vary, determination of optimal ranges of effective amounts of the compound is within the skill of the art. For administration to a human in the curative or prophylactic treatment of the conditions and disorders identified herein, for example, typical dosages of the compounds of the disclosure can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N=dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing a compound disclosed herein can be manufactured in any suitable manner, e.g., by mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all cases the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds as described herein in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the disclosure are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some cases, all the necessary components for the treatment of an PDE4D-related disorder using a compound as disclosed herein either alone or in combination with another agent or intervention traditionally used for the treatment of such disease may be packaged into a kit. Specifically, the disclosure provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Methods of Use of PDE4D Inhibitors

The disclosure further provides methods of using the compounds described herein. In particular, the disclosure provides methods including administering to a subject a compound as described herein and subjecting the subject to an imaging modality. In general, the disclosed method includes contacting PDE4D with a compound or composition disclosed herein in an amount effective to image the subject. In some embodiments, the contacting is in vitro. In other aspects, the contacting is in vivo. In various embodiments, contacting comprises administering the compound or the composition to a subject in need thereof. In embodiments, the subject is a mammal. In embodiments, the mammalian subject is a human.

In embodiments, the administered compound contains an isotopic label, such as $^{11}$C or $^{18}$F. For example, in embodiments, the administered compound can have a structure:
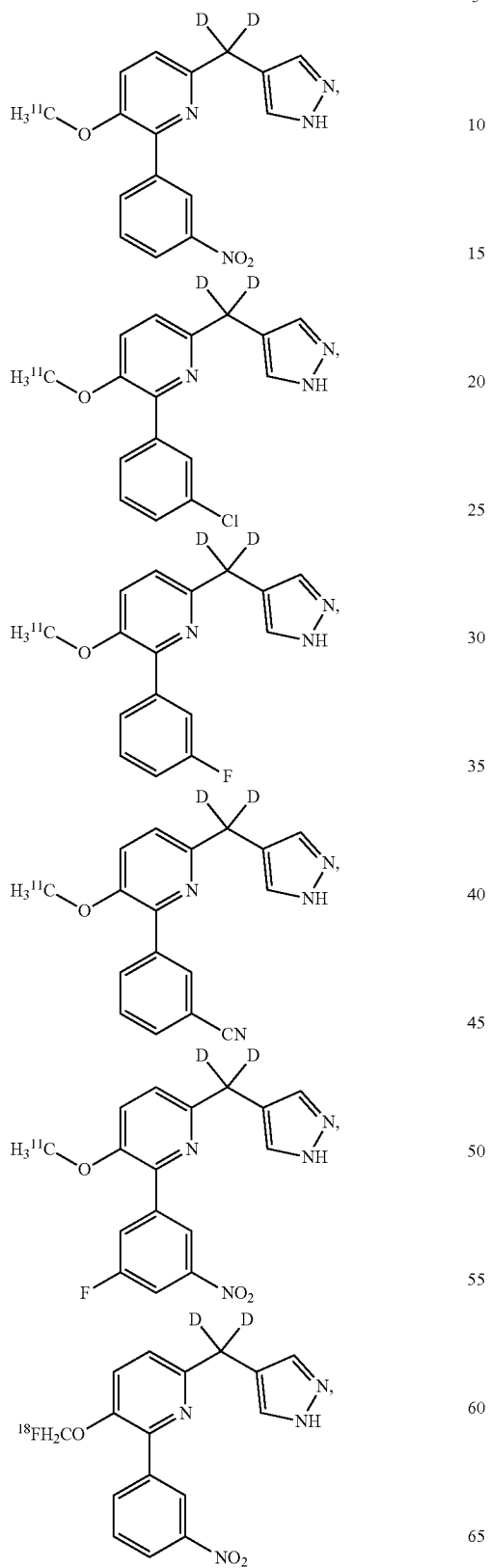
-continued
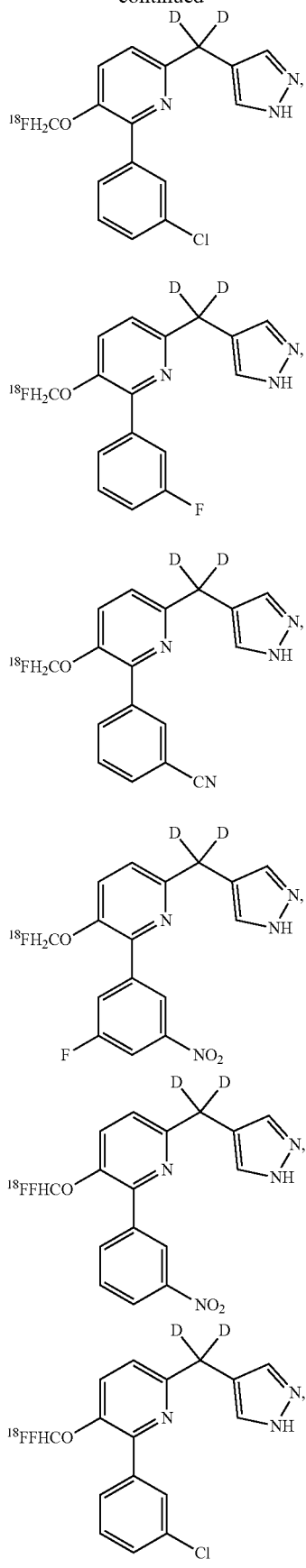

-continued
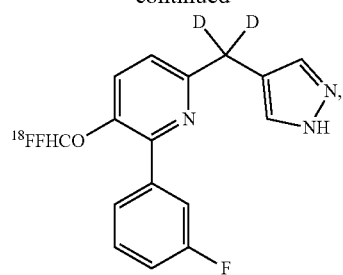
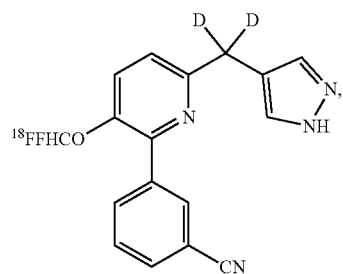
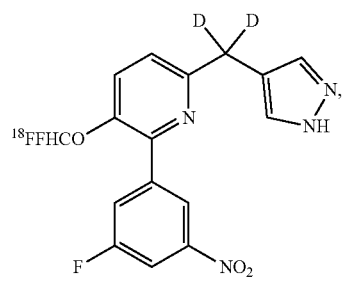
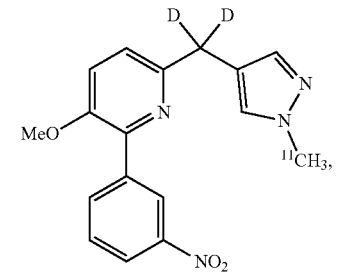
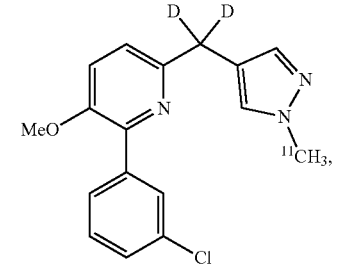
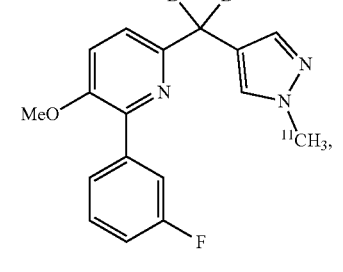
-continued
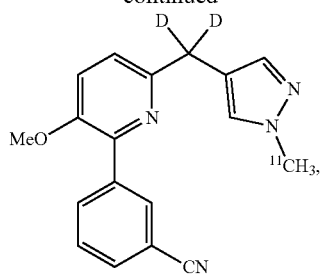
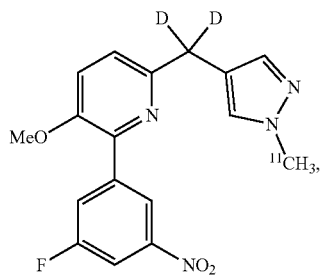
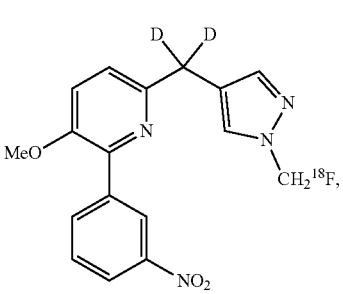
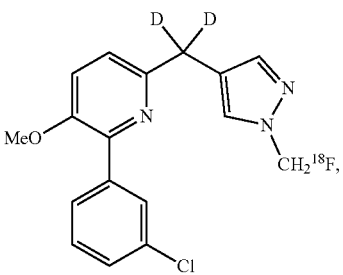
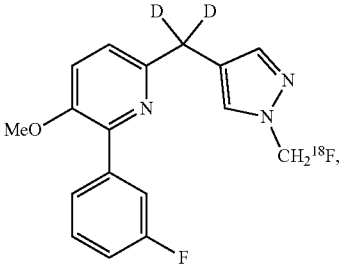
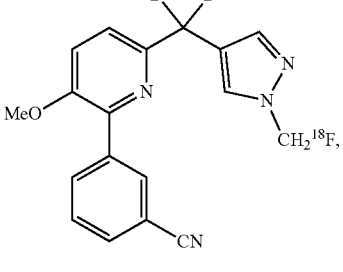

-continued

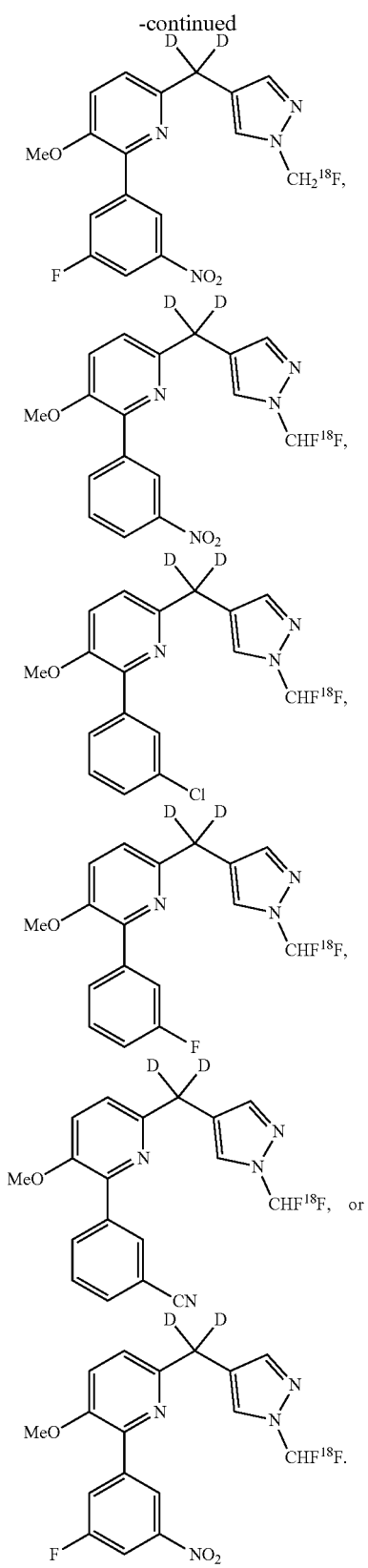

The manner of administration of the compound is not particularly limited. For example, the compound can be prepared in a composition, as described above, and administered intravenously or orally. The manner of administration and dose thereof would be within the purview of the doctor, nurse, or radiologist trained to administer these compounds.

In embodiments, the imaging modality can be selected from positron emission tomography (PET), positron emission tomography/computed tomography (PET/CT), positron emission tomography/magnetic resonance imaging (PET/MRI), planar gamma camera imaging, and/or single-photon emission computerized tomography (SPECT). In some case, the imaging modality is PET.

In embodiments, the subject is subjected to the imaging modality at a point in time ranging from about 5 minutes to 2 hours after of the compound. The time at which the subject is subjected to the imaging modality is dependent on the isotope of the halogen used in the compound. For example, due to the short half-life of $^{18}$F ($t_{1/2}$=about 110 minutes), when the compound is radiofluorinated, the subject can be subjected to the imaging modality at a point in time ranging from about 5 minutes to about 2 hours, about 15 minutes to about 1.75 hours, about 30 minutes to about 1.5 hours, about 45 minutes to about 1.25 hours, or about 50 minutes to about 1 hour, for example at about 5, 10, 15, 20, 25, 30, 35, 40, 45, 50, 55 minutes or 1, 1.10, 1.25, 1.40, 1.50, 1.60, 1.75, 1.80, 1.90, or 2 after administration of the compound. Due to the short half-life of $^{11}$C ($t_{1/2}$=about 20 minutes) when the compound comprises $^{11}$C, the subject can be subjected to the imaging modality at a point in time ranging from about 1 minute to about 30 minutes, about 2 minutes to about 25 minutes, about 5 minutes to about 20 minutes, or about 10 minutes to about 15 minutes, for example about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes after administration of the compound.

In embodiments, the compound inhibits a phosphodiesterase (PDE) isozyme. In embodiments the PDE isozyme is PDE4D. The method as described herein can be used in the imaging of a subject suffering from various conditions. For example, in embodiments, the subject suffers from a condition associated with aberrant PDE activity. Exemplary conditions include, but are not limited to Fragile X syndrome, Alzheimer's disease, memory loss, cognitive dysfunction, autistic spectrum disorder, Parkinson's disease, major depression, bipolar disorder, schizophrenia, multiple sclerosis, traumatic brain injury, or chronic traumatic encephalopathy.

The disclosure further provides methods of treating a subject suffering from a condition associated with aberrant PDE activity. In embodiments, the method of treating comprises administering to the subject a therapeutically effect amount of a compound as described herein, with the proviso that the compound does not comprise $^{11}$C or $^{18}$F.

In general, the disclosed methods include inhibiting PDE4D by a method comprising contacting PDE4D with a compound or composition disclosed herein in an amount effective to inhibit PDE4D. In some embodiments, the contacting is in vitro. In other aspects, the contacting is in vivo. In various embodiments, contacting comprises administering the compound or the composition to a subject in need thereof. In embodiments, the subject is a mammal. In embodiments, the mammalian subject is a human.

In embodiments, the compound inhibits a phosphodiesterase (PDE) isozyme. In embodiments the PDE isozyme is PDE4D. The method as described herein can be used in treating a subject suffering from PDE-related conditions. For example, in embodiments, the subject suffers from a condition associated with aberrant PDE activity. Exemplary conditions include, but are not limited to Fragile X syndrome, Alzheimer's disease, memory loss, cognitive dysfunction, autistic spectrum disorder, Parkinson's disease, major depression, bipolar disorder, schizophrenia, multiple sclerosis, traumatic brain injury, or chronic traumatic encephalopathy.

In certain instances, it may be appropriate to administer at least one of the compounds described herein in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the disclosure with antidepressants, nootropics, anti-acetylcholinesterases, N-methyl D-aspartate (NMDA) receptor antagonists, amyloid beta therapeutics, and tau therapeutics, neurotrophic growth factors, cell based therapies and other regenerative medicine therapies for treatment of neurodegenerative diseases, amongst other therapies which will be apparent to one skilled in the art.

Antidepressants include, for example selective serotonin reuptake inhibitors (SSRIs), such as citalopram, dapoxetine, escitalopram, fluoxetine, fluvoxamine, paroxetine, and sertraline; serotonin-norepinephrine reuptake inhibitors (SN-RIs), such as venlafaxine, desvenlafaxine, minalcipran, levominalcipran, duloxetine, sibutramine, and bicifadine; noradrenergic and specific serotonergic antidepressants (NaSSAs), such as mianserin, mirtazepine, esmirtazepine, and setiptiline; norepinephrine reuptake inhibitors (NRIs), such asatomoxetine, mazindol, reboxetine, esreboxetine, viloxazine, and other specific and nonspecific agents which prevent or mitigate reuptake of norepinephrine (e.g., SNRIs, NDRIs); norepinephrine-dopamine reuptake inhibitors (NDRIs), such as buproprion; selective serotonin reuptake enhancers, such as tianeptine and amineptine; norepinephrine-dopamine disinhibitors (NDDIs), such as agomelatine; tricyclic antidepressants, including tertiary and secondary amine varieties, such as amitriptyline, clomipramine, doxepin, imipramine, trimipramine, desipramine, nortriptyline, and protriptyline; and monoamine oxidase inhibitors (MAOIs), such as isocarboxazid, moclobemide, phenelzine, selegiline, and tranylcyrpomine.

Nootropic drugs, also known as cognition enhancers, can include stimulants, dopaminergics, cholinergics, serotonergics, and many of the antidepressants listed above, as well as certain natural products (e.g., caffeine, tryptophan, 5-HTP, nicotine). Nootropic drugs can also include racetams such as piracetam, pramiracetam, oxiracetam, and aniracetam; amphetamine analogues such as amphetamine (Adderall, Dexedrine), lisdexamfetamine, and methamphetamine; wakefulness enhancers such as modafinil; dopamine reuptake inhibitors such as methylphenidate, and possibly modafinil; acetylcholinesterase inhibitors used to treat Alzheimer's disease such as tacrine, donepezil, galantamine, rivastigmine; NMDA receptor antagonists such as memantine Selective 5-HT6 receptor antagonists such as Lu AE58054; and Nicotinic alpha-7 receptor agonists such as EVP-6124.

In embodiments, the compounds of the disclosure can be co-administered with drugs that reduce nausea, such as Aprepitant (Emend®), Dolasetron (Anzemet®), Granisetron (Kytril®), Ondansetron (Zofran®), Palonosetron (Aloxi®), or Proclorperazine (Compazine®).

Amyloid beta (a-beta or $\alpha\beta$) therapies and tau therapies target the pathological accumulation of a-beta and tau proteins associated with neurodegenerative diseases such as Alzheimer's disease and progressive supernuclear palsy, respectively. A-beta therapies include $\beta$-secretase inhibitors, $\gamma$-secretase inhibitors, $A\beta_{42}$-lowering agents (e.g. tarenflurbil), anti-aggregation agents (e.g. apomorphine), antibodies and other immunotherapies. Tau therapies include Tau phosphorylation inhibitors, tau fibrillization inhibitors, and tau degradation enhancers.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in embodiments, the disclosure provides methods for treating PDE4-mediated disorders in a human or animal subject in need of such treatment comprising administering to said subject an amount of a compound of the disclosure effective to reduce or prevent said disorder in the subject in combination with at least one additional agent for the treatment of said disorder that is known in the art. The disclosure also provides therapeutic compositions comprising at least one compound of the disclosure in combination with one or more additional agents for the treatment of PDE4-mediated disorders.

The compounds of the disclosure can also be useful for the treatment of certain diseases and disorders of the nervous system. Central nervous system disorders in which PDE4 inhibition may be useful include cortical dementias including Alzheimer disease, AIDS-related dementia (HIV dementia), and mild cognitive impairment (MCI). Neurodegenerative disorders in which PDE4 inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and HIV-associated neurodegenerative disorder (HAND), cachexia, Sydenham [S chorea, Huntington[S disease, Parkinson's Disease, amyotrophic lateral sclerosis (ALS), Korsakoff's syndrome, and impairment relating to a cerebral vessel disorder. Further disorders in which PDE4 inhibition might prove useful include neuropathies of the central and peripheral nervous system, including, for example, IgA neuropathy, membranous neuropathy, idiopathic neuropathy, drug-induced peripheral neuropathy, diabetic neuropathy, HIV-associated neuropathy, and chronic inflammatory demyelinating polyneuropathy; as well as transverse myelitis, Gullain-Barre disease, encephalitis, and cancers of the nervous system. Compounds disclosed herein may also be used in the treatment of psychological disorders including anxiety, depression, major depressive disorder (MDD), bipolar disorder, and post-traumatic stress disorder. Compounds disclosed herein may also be used in the treatment of nervous system damage, for example that resulting from stroke, ischemias including cerebral ischemia (both focal ischemia, thrombotic stroke and global ischemia, for example, secondary to cardiac arrest and ischemic heart disease) and ischemia/reperfusion, ototoxicity and hearing loss, acute insults to the inner ear, including acoustic trauma, blast noise (for example, as experienced by military personnel), exposure to ototoxic chemotherapeutic agents for cancer therapy (such as cisplatin) and treatment with aminoglycoside antibiotics and other nervous system trauma.

Compounds disclosed herein may also be used in the treatment of traumatic brain injury (TBI), spinal cord injury (SCl), or a symptom thereof. In certain embodiments, a selective PDE4D inhibitor as disclosed herein will be used to treat SCl, in an amount sufficient to cause a detectable improvement in one or more symptoms, or a reduction in the progression of one or more symptoms of SCl. Additionally, the selective PDE4D inhibitor can be administered in combination with transplantation into the spinal cord of cells. Contemplated cells include stem cells and glial (e.g., Schwann) cells.

Furthermore, compounds of the disclosure may be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds and methods of the disclosure may be useful in the treatment or prevention of drug withdrawal symptoms, for example treatment or prevention of symptoms of withdrawal from opiate, alcohol, or tobacco addiction.

Compounds disclosed herein can also be used in the treatment of acute and chronic pain and inflammation. The compounds of the disclosure may be useful to treat patients with neuropathy, neuropathic pain, or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). The compounds may also be useful in the treatment of pain associated with acute herpes zoster (shingles), postherpetic neuralgia (PHN), and associated pain syndromes such as ocular pain. The compounds may further be useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, pain resulting from cancer, muscular pain, mastalgia, pain resulting from dermal injuries, lower back pain, headaches of various etiologies, including migraine, and the like. The compounds may also be useful for the treatment of pain-related disorders such as tactile allodynia and hyperalgesia. The pain may be somatogenic (either nociceptive or neuropathic), acute and/or chronic. The PDE4 inhibitors of the disclosure may also be useful in conditions where NSAIDs, morphine or fentanyl opiates and/or other opioid analgesics would traditionally be administered.

In addition, compounds disclosed herein may be used in the treatment of insulin resistance and other metabolic disorders such as atherosclerosis that are typically associated with an exaggerated inflammatory signaling.

Compounds disclosed herein may also be used in the treatment of respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; asthma-related diseases such as airway hyperreactivity and small airway disease; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchiolitis, bronchioectasis, cystic fibrosis, pigeon fancier's disease, farmer's lung, acute respiratory distress syndrome, pneumonia, pneumonitis, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, dyspnea, hypercapnea, hyperinflation, hypoxemia, and cough. Further, compounds disclosed herein would find use in the treatment of allergic disorders such as delayed type hypersensitivity reaction, allergic contact dermatitis, allergic rhinitis, and chronic sinusitis.

Compounds disclosed herein may also be used in the treatment of inflammation and related disorders. The compounds disclosed herein may be useful as anti-inflammatory agents with the additional benefit of having significantly less harmful side effects. The compounds may be useful to treat arthritis, including but not limited to rheumatoid arthritis, spondyloarthropathies, gouty arthritis, osteoarthritis, juvenile arthritis, acute rheumatic arthritis, enteropathic arthritis, neuropathic arthritis, psoriatic arthritis, reactive arthritis (Reiter's syndrome), and pyogenic arthritis, and auto immune diseases, including systemic lupus erythematosus, hemolytic syndromes, autoimmune hepatitis, autoimmune neuropathy, vitiligo (autoimmune thyroiditis), Hashimoto's thyroiditis, anemias, myositis including polymyositis, alopecia greata, Goodpasture's syndrome, hypophytis, and pulmonary fibrosis.

Compounds disclosed herein may also be used in the treatment of osteoporosis and other related bone disorders.

Compounds disclosed herein may also be used in the treatment of gastrointestinal conditions such as reflux esophagitis, diarrhea, inflammatory bowel disease, Crohn's disease, gastritis, irritable bowel syndrome, Graves disease disease (hyperthyroidism), necrotizing enterocolitis, and ulcerative colitis. The compounds may also be used in the treatment of pulmonary inflammation, such as that associated with viral infections and cystic fibrosis.

In addition, compounds of the disclosure may also be useful in organ transplant patients either alone or in combination with conventional immunomodulators. Examples of conditions to be treated in said patients include graft vs. host reaction (i.e., graft vs. host disease), allograft rejections (e.g., acute allograft rejection, and chronic allograft rejection), transplant reperfusion injury, and early transplantation rejection (e.g., acute allograft rejection).

Yet further, the compounds of the disclosure may be useful in the treatment of pruritus and vitiligo.

Compounds disclosed herein may also be used in the treatment of tissue damage in such diseases as vascular diseases, migraine headaches, periarteritis nodosa, thyroiditis, aplastic anemia, Hodgkin® disease, sclerodoma, rheumatic fever, type I diabetes, neuromuscular junction disease including myasthenia gravis, white matter disease including multiple sclerosis, sarcoidosis, nephritis, nephrotic syndrome, Langerhan cell histiocytosis cell histiocytosis, glomerulonephritis, reperfusion injury, pancreatitis, interstitial cystitis, Behcet's syndrome, polymyositis, gingivitis, periodontis, hypersensitivity, swelling occurring after injury, ischemias including myocardial ischemia, cardiovascular ischemia, and ischemia secondary to cardiac arrest, cirrhosis, septic shock, endotoxic shock, gram negative sepsis, toxic shock syndrome, stroke, ischemia reperfusion injury, multi-organ dysfunction, restenosis including restenosis following coronary bypass surgery, and the like. The compounds disclosed herein can be used in the treatment of various stages and/or types of multiple sclerosis, such as, relapsing-remitting forms of multiple sclerosis, progressive multiple sclerosis, and remyelination in multiple sclerosis.

Furthermore, the compounds disclosed herein may also be useful in inhibiting PDE4 activity for the amelioration of systemic disorders including systemic hypotension associated with septic and/or toxic hemorrhagic shock induced by a wide variety of agents; as a therapy with cytokines such as TNF, IL-1 and IL-2; and as an adjuvant to short term immunosuppression in transplant therapy.

Compounds disclosed herein may also be used in the treatment of cancer, such as colorectal cancer, and cancer of the breast, lung, prostate, bladder, cervix and skin. Compounds of the disclosure may be used in the treatment and prevention of neoplasias including but not limited to brain cancer, bone cancer, leukemia, lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods may also be used to treat the fibrosis which occurs with radiation therapy. The present compounds and methods may be used to treat subjects having adenomatous polyps, including those with familial adenomatous polyposis (FAP). Additionally, the present compounds and methods may be used to prevent polyps from forming in patients at risk of FAP.

Compounds disclosed herein may also be used in the treatment of otic diseases and otic allergic disorders, including eustachian tube itching.

Compounds disclosed herein may also be used in the treatment of ophthalmic diseases, such as ophthalmic allergic disorders, including allergic conjunctivitis, vernal conjunctivitis, vernal keratoconjunctivitis, and giant papillary conjunctivitis, dry eye, glaucoma, corneal neovascularization, optic neuritis, Sjogren's syndrome, retinal ganglion degeneration, ocular ischemia, retinitis, retinopathies, uveitis, ocular photophobia, and of inflammation and pain associated with acute injury to the eye tissue. Specifically, the compounds may be used to treat glaucomatous retinopathy and/or diabetic retinopathy. The compounds may also be used to treat post-operative inflammation or pain as from ophthalmic surgery such as cataract surgery and refractive surgery. In certain embodiments, the compounds of the disclosure are used to treat an allergic eye disease chosen from allergic conjunctivitis; vernal conjunctivitis; vernal keratoconjunctivitis; and giant papillary conjunctivitis.

Moreover, compounds of the disclosure may be used in the treatment of menstrual cramps, dysmenorrhea, premature labor, endometriosis, tendonitis, bursitis, skin-related conditions such as psoriasis, eczema, burns, sunburn, dermatitis, pancreatitis, hepatitis, lichen planus, scleritis, scleroderma, dermatomyositis, and the like. Other conditions in which the compounds of the disclosure can be used include diabetes (type I or type II), atherosclerosis, congestive heart failure, myocarditis, atherosclerosis, cerebral ischemia, angiogenesis, pulmonary hypertension, and aortic aneurysm.

The compounds disclosed herein may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. Additional co-therapies comprising the compounds disclosed herein with biologics include: tumor necrosis factor alpha (TNFα) blockers such as etanercept (Enbrel), infliximab (Remicade), adalimumab (Humira), certolizumab pegol (Cimzia), and golimumab (Simponi); Interleukin 1 (IL-1) blockers such as anakinra (Kineret); monoclonal antibodies against B cells such as rituximab (Rituxan); T cell costimulation blocker such as abatacept (Orencia); and Interleukin 6 (IL-6) blockers such as tocilizumab (RoActemra or Actemra, an anti-IL-6 receptor antibody).

Compounds disclosed herein may also be used to prevent tissue damage when therapeutically combined with antibacterial or antiviral agents. In certain embodiments, the compounds disclosed herein may be combined with neuraminidase inhibitors for the treatment of a viral disease such as influenza.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compounds that are suitable for use in treating subjects suffering from a condition associated with aberrant PDE activity do not comprise $^{11}C$ or $^{18}F$. Examples of suitable compounds include, but are not limited to:

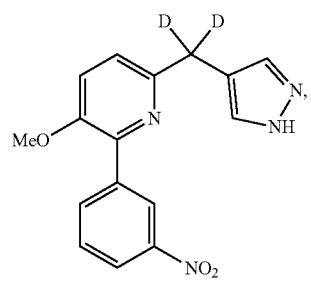

-continued

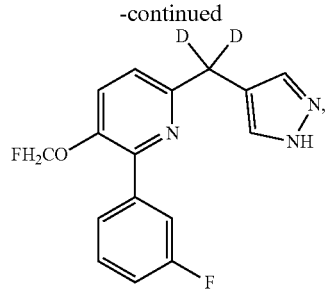
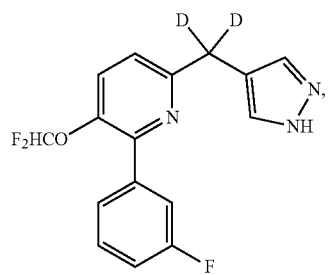
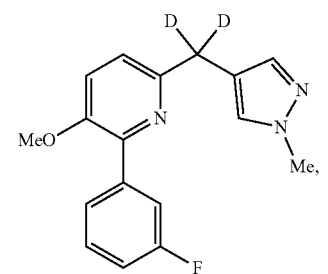
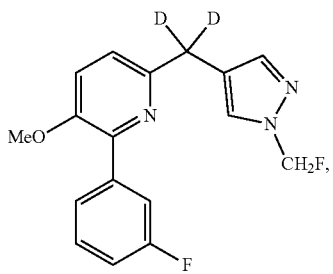
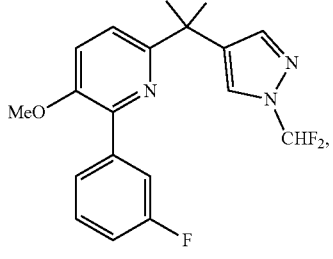
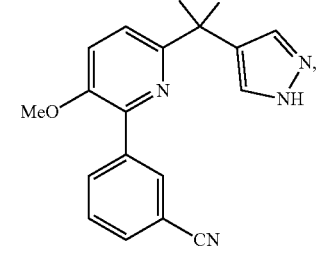
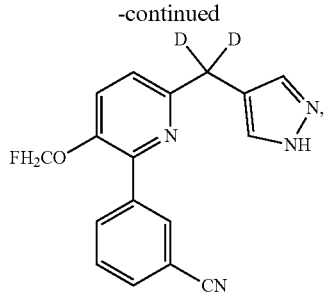
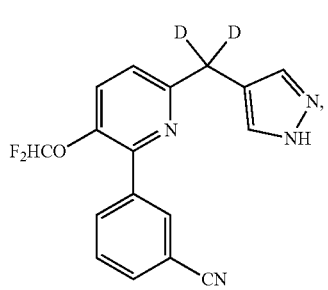
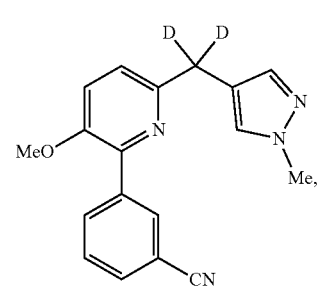
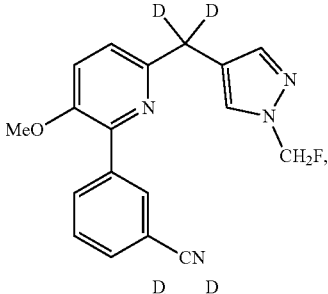
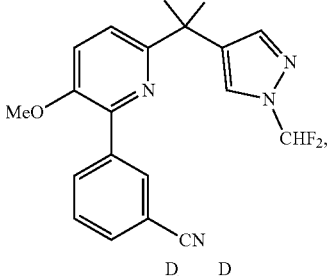
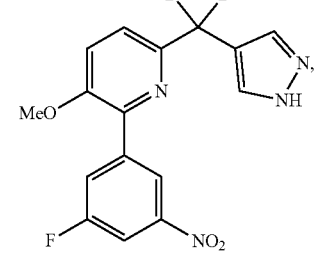

-continued

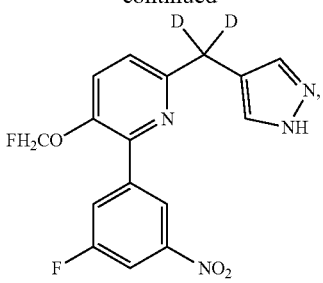

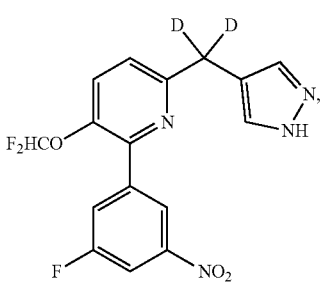

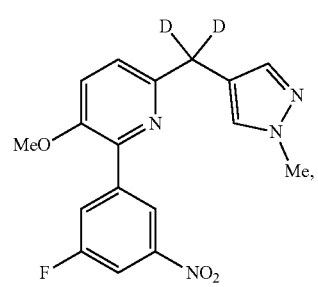

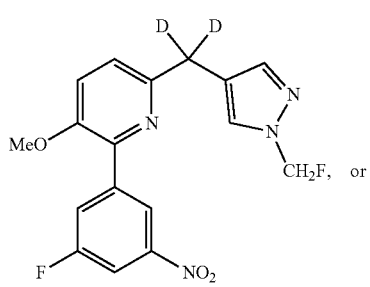

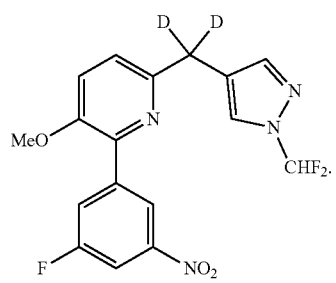

In some cases, the compound is:

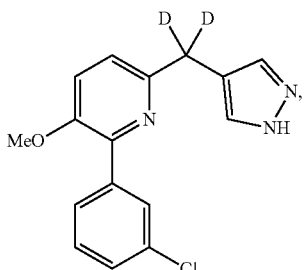

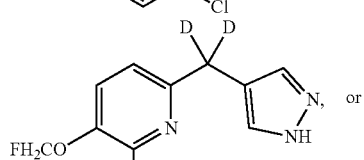

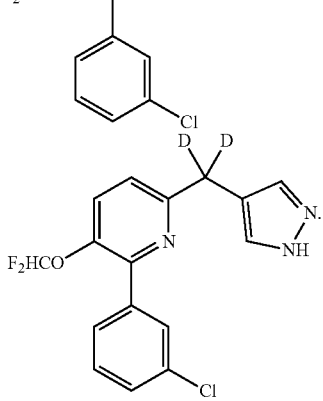

Synthesis of PDE4D Inhibitors

Compounds as disclosed herein can be prepared via a variety of synthetic means. Guidance is provided to the synthetic organic chemist in view of the below general discussion as well as the specific procedures provided in the Examples section.

The compounds provided herein can be synthesized using conventional techniques readily available starting materials known to those skilled in the art. In general, the compounds provided herein are conveniently obtained via standard organic chemistry synthesis methods.

Although not limited to any one or several sources, classic texts such as Smith, M. B., March, J., March[S]s Advanced Organic Chemistry: Reactions, Mechanisms, and Structure, 5$^{th}$ edition, John Wiley & Sons: New York, 2001; and Greene, T. W., Wuts, P. G. M., Protective Groups in Organic Synthesis, 3$^{rd}$ edition, John Wiley & Sons: New York, 1999, are useful and recognized reference textbooks of organic synthesis known to those in the art. The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt thereof.

In general, the compounds of Formula (I) can be synthesized in line with the examples shown below. For instance, the compounds can be prepared by alkylating an appropriate pyridinecarboxylic acid, with protecting groups as necessary. The alkylated pyridinecarboxylic acid can then be deuterated and coupled to an appropriate pyrazole to obtain a desired compound of Formula (I). Further modifications can be performed, e.g. to introduce additional substituent groups, such as alkyl, hydroxyl, nitro, and/or halo groups.

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

Example 1

Compound Synthesis

Preparation of Compound 1: 3-methoxy-2-(3-nitrophenyl)-6-[(1H-pyrazol-4-yl)($^2H_2$)methyl]pyridine Step 1: 2-Bromo-3-methoxy-6-pyridinecarboxylic acid (500 mg, 2.16 mmol) was dissolved in MeOH (10 mL), treated with TMS-Cl (550 uL, 4.3 mmol) and stirred at room temperature for 22 hrs. The reaction was concentrated to dryness to give methyl 2-bromo-3-methoxy-6-pyridinecarboxylic acid. $^1H$ NMR (CDCl$_3$) δ 3.99 (s, 3H), 4.01 (s, 3H), 7.22 (d, J=8.4 Hz, 1H), 8.12 (d, J=8.3 Hz, 1H).

Step 2: Methyl 2-bromo-3-methoxy-6-pyridinecarboxylic acid (1.4 g, 5.69 mmol) was dissolved in THF (80 mL), then treated with NaBD$_4$ (1.43 g, 34.1 mmol) and heated to reflux. CH$_3$OD (10 mL) was added and the reaction heated for 2.5 hrs. After cooling to room temperuture, the reaction was quenched with NH$_4$Cl and extracted with EtOAc (2×80 mL). The organic phases were dried with Na$_2$SO$_4$ and concentrated. It was chromatographed on silica gel (0-5% acetone/DCM) to give 2-bromo-3-methoxy-6-(dideuteriohydroxymethyl)pyridine. $^1H$ NMR (CDCl$_3$) δ ppm 7.24 (s, 2H), 3.93 (s, 3H), 2.81 (brd s, 1H).

Step 3: 2-Bromo-3-methoxy-6-(dideuteriohydroxymethyl)pyridine (1.30 g, 5.9 mmol) was dissolved in dioxane (35 mL), then treated with 3-nitro phenyl boronic acid (1.20 g, 7.1 mmol), silica support Pd (Silicycle SiliCat DPP-Pd, 1.0 g, 0.3 mmol), and K$_3$PO$_4$ (2.0 g, 9.4 mmol). The reaction was purged with Ar for 5 min, then heated to 90° C. under Ar. After 16 hrs, the reaction was cooled to room temperature and diluted with EtOAc (35 mL). The reaction was filtered through Celite and the pad washed well with EtOAc. The combined organics were filtered and concentrated to give 2-(3-nitro-phenyl)-3-methoxy-6-(dideuteriohydroxymethyl)pyridine (1.76 g) which was used without further purification.

Step 4: Crude 2-(3-nitro-phenyl)-3-methoxy-6-(dideuteriohydroxymethyl)pyridine (1.76 g) was dissolved in DCM (60 mL), cooled to 0° C., and treated with PBr$_3$ (1.2 mL, 12.6 mmol). The reaction was allowed to slowly warm to room temperature and stirred overnight. After 16 hrs, the reaction was poured onto saturated NaHCO$_3$ at 0° C. The phases were separated, and the aqueous phase extracted 2× DCM (70 mL). The combined organic phases were dried with Na$_2$SO$_4$ and concentrated to give 2-(3-nitro-phenyl)-3-methoxy-6-(dideuteriomethylbromide)pyridine (1.83 g), which was used without further purification.

Step 5: Crude 2-(3-nitro-phenyl)-3-methoxy-6-(dideuteriomethylbromide)pyridine (1.00 g, 3.22 mmol) was dissolved in dioxane/water (4:1, 15 mL) and treated with 1-(1-ethoxyethyl)-4-(4,4,5,5-tetramethyl-1,3,2-dioxaborolan-2-yl)-1H-pyrazole (1.3 g, 4.83 mmol), Pd(dppf)$_2$Cl$_2$*DCM (200 mg, 0.25 mmol), and K$_3$PO$_4$ (1.4 g, 6.6 mmol). The reaction was purged with Ar for 5 min, then heated to 90° C. under Ar for 20 hrs. The reaction was diluted with water (50 mL) and filtered through Celite to remove insoluble materials. Crude product was extracted with EtOAc and the solvent then evaporated. The residue was taken up in MeOH (10 mL) and 2N HCl (6 mL) and stirred overnight. The reaction was neutralized with NaHCO$_3$, then extracted 3× EtOAc. The combined organics were washed 1× brine, dried with Na$_2$SO$_4$, and concentrated. The sample was purified by preparative TLC with 3-5% EtOAc/DCM as eluent to give 3-methoxy-2-(3-nitrophenyl)-6-[(1H-pyrazol-4-yl)($^2H_2$)methyl]pyridine (Compound 1). $^1H$ NMR (CDCl$_3$) δ 7.17 (d, J=8.6 Hz, 1H), 7.29 (d, J=8.6 Hz, 1H), 7.56 (s, 2H), 7.62 (t, J=8.01 Hz, 1H), 8.25 (ddd, J=8.2, 2.3, 1.0 Hz, 1H), 8.37 (dt, J=7.8, 1.3 Hz, 1H), 8.91 (t, J=2 Hz, 1H)

Preparation of Compound 2: 2-(3-nitrophenyl)-6-[(1H-pyrazol-4-yl)($^2H_2$)methyl]pyridin-3-ol Compound 1 (70 mg, 0.22 mmol), 48% HBr (1.2 mL), and HOAc (0.12 mL) were heated to 130° C. for 17 hrs. After cooling, the reaction was quenched with saturated NaHCO3 and extracted 3× EtOAc. The combined organic phases were washed with brine, dried with Na$_2$SO$_4$, and concentrated. The solid was then triturated with hot acetonitrile (6 mL), then chromatographed (10% acetone/DCM) to give Compound 2. $^1H$ NMR (DMSO-d$_6$) δ ppm 7.14 (d, J=8.3 Hz, 1H), 7.33 (d, J=8.3 Hz, 1H), 7.41 (brd s, 1H), 7.57 (brd s, 1H), 7.75 (t, J=8.1 Hz, 1H), 8.22 (ddd, J=8.2, 2.4, 1.0 Hz, 1H), 8.57 (dt, J=7.9, 1.3 Hz, 1H), 8.96 (t, J=2.0 Hz, 1H), 10.37 (s, 1H), 12.59 (brd s, 1H).

Preparation of Compound 3: 2-(3-chlorophenyl)-3-(difluoromethoxy)-6-[(1H-pyrazol-4-yl)($^2H_2$)methyl]pyridine Step 1: Methyl 2-bromo-3-hydroxy-6-pyridinecarboxylic acid (200 mg, 0.865 mmol) and sodium chlorodifluoroacetate (400 mg, 2.62 mmol) were dissolved in DMF (7 mL), then treated with Na$_2$CO$_3$ (880 mg, 2.70 mmol) and heated to 60° C. for 5 hrs. After cooling to room temperature, the reaction was diluted with water and extracted 3× EtOAc. The combined organics were dried with Na$_2$SO$_4$ and concentrated. Methyl 2-bromo-3-difluoromethoxy-6-pyridinecarboxylic acid was purified by chromatography (DCM/hexanes 1.5:1).

Step 2: Methyl 2-bromo-3-difluoromethoxy-6-pyridinecarboxylic acid (280 mg, 1.0 mmol) was dissolved in methanol-d$_4$ (2 ml) and treated with NaBD$_4$ (200 mg, 4.76 mmol). After stirring at 45° C. for 2.5 hrs, the reaction was quenched with NH$_4$Cl and extracted with DCM. The organics were dried with Na$_2$SO$_4$ and concentrated. The crude was purified by chromatography (1% MeOH/DCM) to give [6-bromo-5-(difluoromethoxy)pyridin-2-yl]($^2H_2$)methanol. $^1H$ NMR (DMSO-d$_6$) δ ppm 7.79 (d, J=8.3 Hz, 1H), 7.55 (d, J=8.3 Hz, 1H), 7.23 (t, 73 Hz, 1H). 5.56 (s, 1H).

Step 3: [6-Bromo-5-(difluoromethoxy)pyridin-2-yl]($^2H_2$)methanol (75 mg, 0.29 mmol), 3-chlorophenyl-boronic acid (90 mg, 0.58 mmol), K$_3$PO$_4$ (130 mg, 0.61 mmol), and Pd(dppf)Cl$_2$ (25 mg, 0.03 mmol) were suspended in dioxane/H2O (4:1, 2 mL), purged with Ar for 10 min, then heated to 90° C. for 20 hrs. After cooling to room temperature, the reaction was diluted with EtOAc and H$_2$O, then filtered through a plug of Celite. The filtrate was extracted with EtOAc, and the organics were dried with $Na_2SO_4$, and concentrated. The crude was purified by silica gel chromatography (DCM) to afford [6-(3-chlorophenyl)-5-(difluoromethoxy)pyridin-2-yl]($^2H_2$)methanol. $^1H$ NMR (DMSO-$d_6$) δ ppm 7.80 (m, 4H), 7.54 (m, 4H), 7.26 (t, J=73 HZ, 1H), 5.49 (s, 1H).

Step 4: [6-(3-Chlorophenyl)-5-(difluoromethoxy)pyridin-2-yl]($^2H_2$)methanol (76 mg, 0.26 mmol) in DCM (2 mL) was treated at 0° C. with $PBr_3$ (50 uL, 0.53 mmol) then stirred at room temperature overnight. The crude reaction was poured onto ice/$NaHCO_3$ and extracted 3× DCM. The combined organics were washed with $H_2O$ and brine, dried with $Na_2SO_4$ and concentrated to yield 6-[bromo($^2H_2$)methyl]-2-(3-chlorophenyl)-3-(difluoromethoxy)pyridine.

Step 5: Crude 6-[bromo($^2H_2$)methyl]-2-(3-chlorophenyl)-3-(difluoromethoxy)pyridine (80 mg, 0.23 mmol) was dissolved in dioxane/water (4:1, 1.5 mL) and treated with 1-(1-ethoxyethyl)-4-(4,4,5,5-tetramethyl-1,3,2-dioxaborolan-2-yl)-1H-pyrazole (110 mg, 0.34 mmol), Pd(dppf)$_2$Cl$_2$*DCM (20 mg, 0.025 mmol), and $K_3PO_4$ (100 mg, 0.47 mmol). The reaction was purged with Ar for 5 min, then heated to 85° C. under Ar for 20 hrs. The reaction was diluted with water (50 mL) and filtered through Celite to remove insoluble materials. Crude product was extracted with EtOAc and the solvent then evaporated. The residue was taken up in MeOH and 2N HCl and stirred overnight. The reaction was neutralized with $NaHCO_3$, then extracted 3× EtOAc. The combined organics were washed with brine, dried with $Na_2SO_4$, and concentrated. The sample was purified by chromatography (3-5% EtOAc/DCM, then 4:1 hexane/acetone) to give Compound 3. $^1H$ NMR (CDCl$_3$) δ ppm 7.88 (t, J=1.7 Hz, 1H), 7.77 (m, 1H), 7.60 (m, 3H), 7.43 (m, 2H), 6.99 (d, J=8.4 Hz, 1H), 6.42 (t, J=73 Hz, 1H), 6.38 (t, J=2.1 Hz, 1H).

Radioligand Compound Procedure—Preparation of Compound A

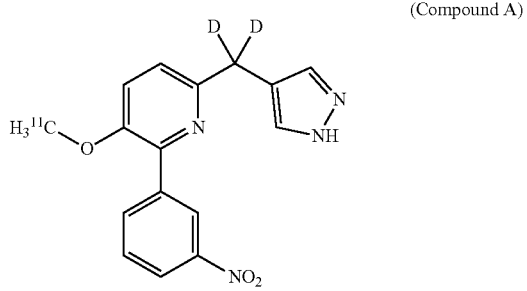 [SMILES: [2H]C([2H])(c1cn[nH]c1)c1ccc(O[11CH3])c(-c2cccc([N+](=O)[O-])c2)n1]
(Compound A)

[$^{11}C$]—$CO_2$ was prepared via a $^{14}N[p,α]^{11}C$ nuclear reaction on a Siemens RDS-111 cyclotron, using 1% $O_2$ in $N_2$ (UHP 500, Airgas) as the target gas, using a Havar HP target (aluminum, volume=9.5 mL). The target was loaded to 280 psi, then irradiated at 60 μA for 20 minutes. The target was then emptied to a soda lime trap. For production, the target was irradiated for approximately 40 min at 60 μA. Target yield was about 1400 mCi.

[$^{11}C$] methyl iodide was produced under standard conditions. First, reduction of the [$^{11}C$]—$CO_2$ using a Ni-Shimalite catalyst under hydrogen atomosphere at 350° C. to produce $^{11}C$-methane, which was trapped on a carboxen trap at −75° C., release with warming and converted to [$^{11}C$] methyl iodide by recirculation for 5 minutes over a quartz oven for iodination at 750° C. Following trapping on a Porapak Q column, the [$^{11}C$]-methyl iodide was released at 190° C. at a helium flow rate of 20 mL/min and bubbled into a reactor vessel pre-charged with 1 μL 3 M sodium hydroxide combined with a solution of

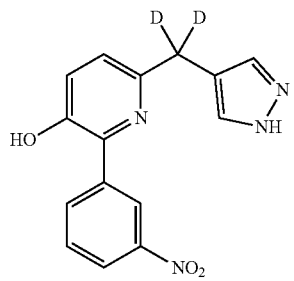 [SMILES: [2H]C([2H])(c1cn[nH]c1)c1ccc(O)c(-c2cccc([N+](=O)[O-])c2)n1]

in anhydrous DMF held at 25° C. Upon completion of this transfer, the reactor vessel was heated to 90° C. for 5 min, then semi-prep HPLC eluent was added (55:45 50 mM Ammonium formate pH 8.0: Acetonitrile), and the resulting solution was injected into an HPLC equipped with a Agilent Eclipse XDB C18, 9.4'250 mm, 10 μm column for purification. Compound A was obtained.

Example 2

Biological Testing

PET Scanning

The regional distribution and pharmacokinetics of $^{11}C$-labeled compounds as described herein were evaluated on non-human primates via PET imaging.

Two male non-naïve cynomolgus non-human primates (*Macaca fascicularis*) ("Subject 1" and "Subject 2") were utilized in this study (7.0 and 5.5 kg). Subjects had previously undergone surgery for placement of arterial access ports for blood collection from the iliac artery. Each subject underwent a brain MR in a Philips 1.5T Intera scanner using a 3D T1 FFE sequence for subsequent registration with PET and application of a cynomolgus brain region of interest atlas for determination of regional time-activity curves. PET scans were conducted in each subject under baseline condition (i.e., Compound A, only) and 15 minutes after a 10 minute infusion of Compound B at 3 mg/kg (i.e. blocking condition). Compound B is a known PDE4D ligand, alternatively referred to as BPN14770.

(Compound A)

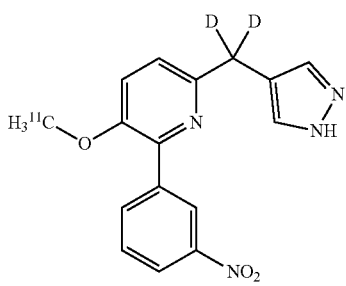

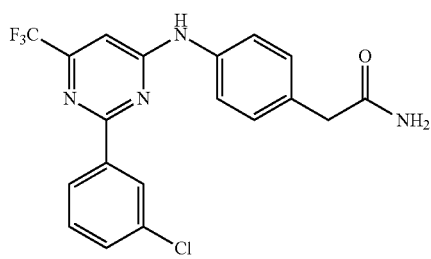

(Compound B)

PET scans were conducted with a Siemens Focus 220 microPET scanner. Subjects were anesthetized with ketamine 10 mg/kg IM approximately 45 minutes prior to Compound A injection. Atropine sulfate 0.05 mg/kg IM was administered approximately 35 minutes prior to Compound A injection. Subjects were intubated and maintained on isoflurane (2-2.5%) and oxygen (2 L/min). Indwelling catheters were placed in the saphenous veins for drug infusion, tracer injection and fluids (LRS 10 mL/kg/hr IV). Subjects were transported to the PET imaging bed, positioned, and monitored for body temperature, heart rate, expired $CO_2$, respiration rate, and pulse $O_2$.

A dynamic 90 (Subject 1) or 120 (Subject 2) minute PET scan acquisition was initiated at the start of Compound A injection, administered over 3 minutes via an infusion pump targeting an injected activity of 5 mCi. Relative to time of Compound A injection, arterial blood samples were collected in $K_2EDTA$ at −10, 0.75, 1.5, 2.25, 3, 4, 5, 10, 15, 30, 45, 60, 90 and 120 min. For each sample, an aliquot (200 uL) was gamma counted for radioactivity concentration determination, then processed to plasma. For −10, 5, 15, 30, 60, 90, 120 min plasma samples, radio HPLC was performed for determination of parent fraction of Compound A, and −10 min samples spiked with Compound A were used for stability analysis and determination of plasma free fraction. Aliquots (100 uL) of plasma samples collected at −10, 5, 15, 30, 60, 90, 120 min were frozen for subsequent determination of drug concentration levels. Table 1 shows the radioactive dose conditions for the Subjects.

TABLE 1

| | PET Scan Dosage Summary | | | |
|---|---|---|---|---|
| Subject | Condition | Dose Radioactivity (mCi) | Scan Duration (min) | $f_p$ (%)[†] |
| 1 | baseline | 3.2 | 90 | 5.9 |
| | blocking | 5.3 | | 5.9 |
| 2 | baseline | 5.4 | 120 | 6.7 |
| | blocking | 4.2 | | 4.7 |

[†]Plasma free fraction?

At the conclusion of PET scan acquisition, an x-ray CT scan by an 8 slice NeuroLogica CereTom OTOscan of each Subject was collected of the head at 120 kVp, 4 mAs, slice thickness 0.625 mm and processed using filtered back projection. The CT scan was used for co-registration to PET for attenuation and scatter correction of the reconstructed PET scan. Listmode PET data were binned into 6×0.5 min, 3×1 min, 2×2 min and 22 ×5 min frames. Binned sinogram data were reconstructed by filtered backprojection.

PET Image Analysis

Reconstructed PET images were analyzed using PMOD software. PET scans were transformed into MR template space via rigid PET-to-MR and affine+nonlinear MR-to-template registrations. Time-activity curves were generated from regions of interest (ROIs) defined on the MR template including the anterior cingulate, cerebellum, dorsolateral prefrontal cortex, entorhinal cortex, occipital cortex, striatum and thalamus. Peak uptake in the brain was between about 3.2% and 5.6% of the injected dose.

Volume of distribution ($V_T$) (mL/cm$^3$) of Compound A was estimated with the 2-tissue compartment (2TC) model and Logan graphical analysis (LGA, t*=30), for baseline and blocking scans, using 90 min of data. $V_T$ at baseline and blocking in ROIs were used to compute occupancy of Compound B via the occupancy (Lassen) plot. Time stability of $V_T$ estimated from 2TC and LGA models were assessed for both animals from 90 min or 120 minutes of data for baseline and blocking scans. Table 2 shows Compound A $V_T$ of the various tested regions of the brain under the two models. Table 3 shows the occupancy of Compound B under the two models.

TABLE 2

Compound A $V_T$ in mL/cm$^3$ after 90 Minutes of PET Scanning

| | Subject 1 | | | | Subject 2 | | | |
|---|---|---|---|---|---|---|---|---|
| | 2TC | | LGA | | 2TC | | LGA | |
| Region | baseline | blocking | baseline | blocking | baseline | blocking | baseline | blocking |
| Anterior Cingulate | 15.8 | 8.8 | 13.8 | 8.9 | 13.7 | 10.6 | 14.6 | 10.4 |
| Cerebellum | 11.5 | 7.6 | 10.2 | 7.7 | 8.6 | 9.6 | 9.2 | 9.7 |
| Dorsolateral Frontal Cortex | 26.2 | 10.2 | 22.9 | 10.1 | 15.2 | 12.3 | 15.5 | 10.6 |
| Enthorinal Cortex | 14.6 | 8.1 | 11.7 | 7.4 | 10.8 | 10.1 | 10.5 | 7.8 |
| Hippocampus | 30.3 | 7.4 | 19.4 | 7.5 | 19.8 | 11.1 | 17.4 | 11.0 |
| Occipital Cortex | 17.8 | 8.4 | 15.1 | 8.0 | 12.9 | 10.6 | 13.1 | 10.0 |
| Striatum | 14.9 | 9.0 | 13.9 | 9.2 | 13.2 | 11.5 | 13.4 | 11.2 |
| Thalamus | 17.6 | 8.8 | 15.7 | 8.9 | 11.6 | 9.9 | 12.1 | 9.8 |

TABLE 3

| | Compound B Occupancy | |
|---|---|---|
| Subject | Model | Occupancy (%) |
| 1 | 2TC | 84 |
| | LGA | 88 |
| 2 | 2TC | 82 |
| | LGA | 73 |

The PET image analysis demonstrated that Compound A readily entered the brain, and regional uptake was consistent with the known distribution of Compound B. Further, the blockage of PDE4D with a high dose of Compound B led to a substantial reduction of Compound A in regions of high uptake.

What is claimed is:

1. A compound having the structure of Formula (I):

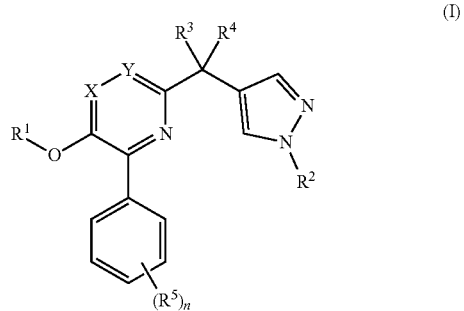

(I)

wherein
$R^1$ is H, $C_{1-6}$ alkyl, or $C_{1-6}$ haloalkyl;
$R^2$ is H, $C_{1-3}$ alkyl, or $C_{1-3}$ haloalkyl;
$R^3$ and $R^4$ are each H or D, and at least one of $R^3$ and $R^4$ is D;
each $R^5$ is independently halo, CN, OH, $NO_2$, $C_{1-6}$ alkoxy, $C_{1-6}$ haloalkoxy, $C_{1-6}$ alkyl, $C_{1-6}$ haloalkyl, O-$C_{3-6}$ cycloalkyl, $C_{1-6}$ hydroxyalkyl, or $SO_2$-$C_{1-3}$ alkyl;
X and Y are each independently $CR^6$ or N;
each $R^6$ is independently H, $C_{1-3}$ alkyl, or $C_{1-3}$ haloalkyl; and
n is 0, 1, 2, 3, or 4,
or a pharmaceutically acceptable salt thereof.

2. The compound of claim 1, wherein $R^1$ is $C_{1-6}$ alkyl and at least one carbon of the $C_{1-6}$ alkyl is $^{11}C$.

3. The compound of claim 2, wherein $R^1$ is $^{11}CH_3$.

4. The compound of claim 1, wherein $R^1$ is H.

5. The compound of claim 1, wherein $R^1$ is $CH_3$.

6. The compound of claim 1, wherein $R^1$ is $CH_2F$ or $CHF_2$.

7. The compound of claim 6, wherein $R^1$ is $CH_2^{18}F$, $CHF^{18}F$, or $CH(^{18}F)_2$.

8. The compound of claim 1, wherein $R^2$ is $C_{1-3}$ alkyl and at least one carbon of the $C_{1-3}$ alkyl is $^{11}C$.

9. The compound of claim 8, wherein $R^2$ is $^{11}CH_3$.

10. The compound of claim 1, wherein $R^2$ is H.

11. The compound of claim 1, wherein $R^2$ is $CH_3$.

12. The compound of claim 1, wherein $R^2$ is $CH_2F$ or $CHF_2$.

13. The compound of claim 12, wherein $R^2$ is $CH_2^{18}F$, $CHF^{18}F$, or $CH(^{18}F)_2$.

14. The compound of claim 1, wherein each of $R^3$ and $R^4$ is D.

15. The compound of claim 1, wherein at least one $R^5$ is $NO_2$, halo, or CN.

16. The compound of claim 1, wherein n is 1 or 2.

17. The compound of claim 16, wherein n is 2, one $R^5$ is F and the other is $NO_2$.

18. The compound of claim 17, where F is $^{18}F$.

19. The compound of claim 1, wherein X is CH.

20. The compound of claim 1, wherein Y is CH.

21. The compound of claim 1, having a structure selected from the group consisting of:

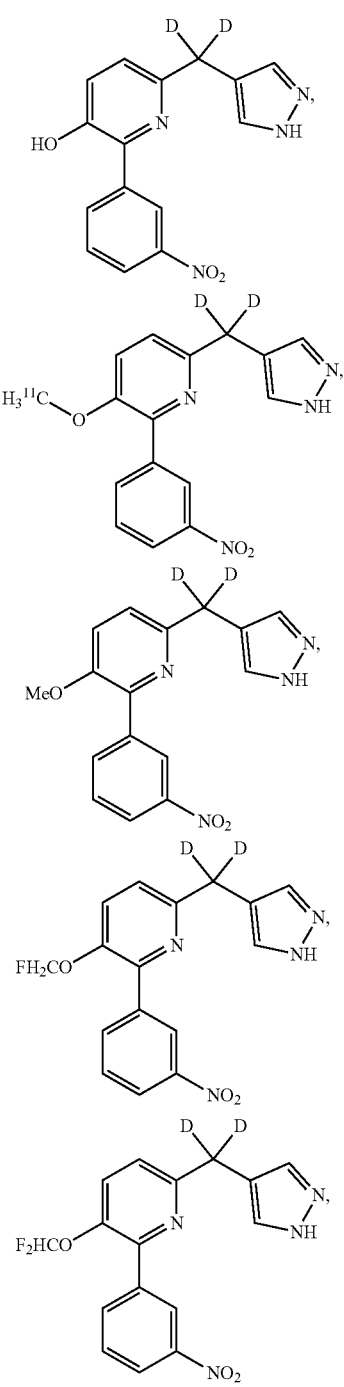

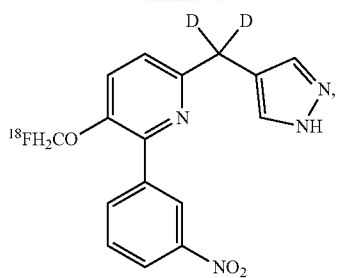
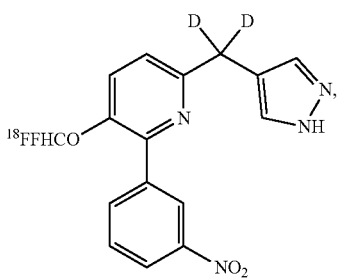
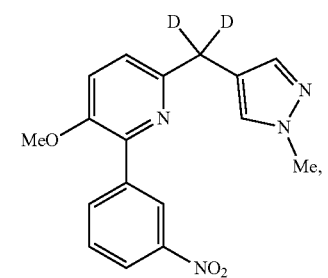
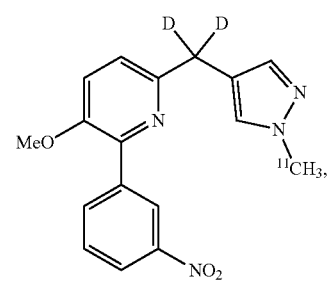
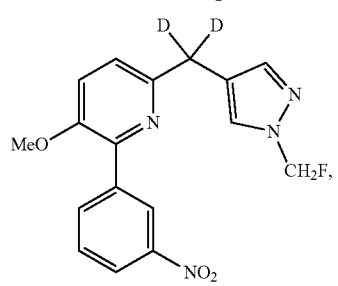
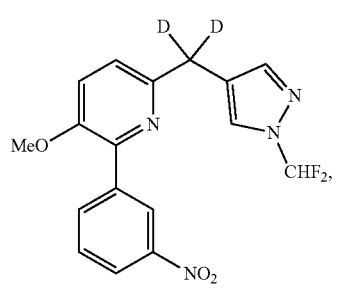
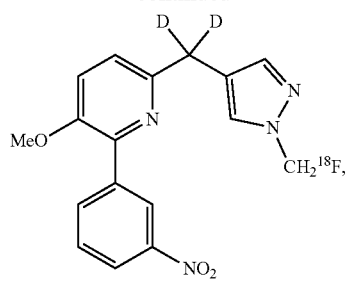
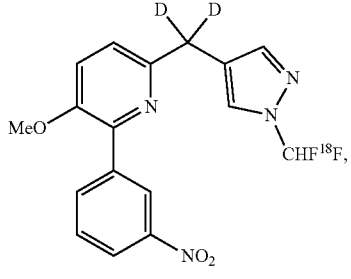
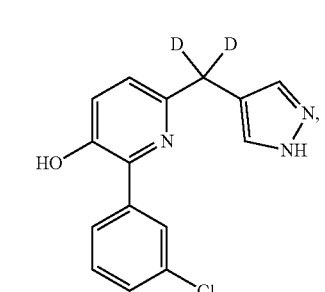
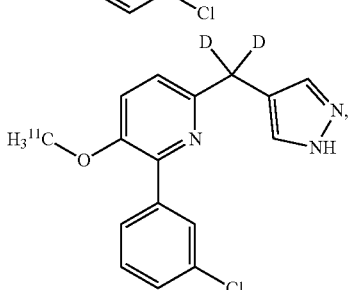
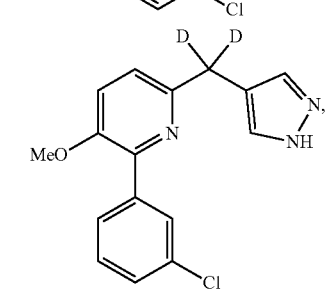
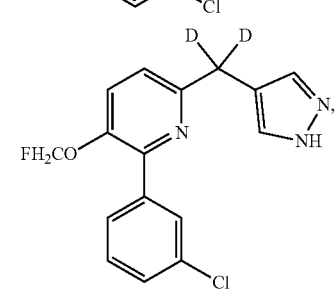

-continued
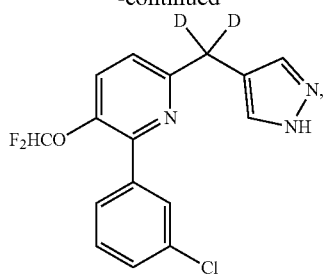
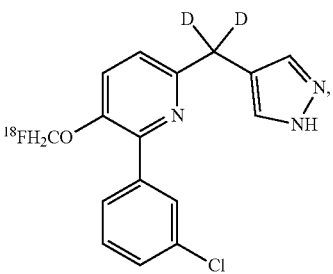
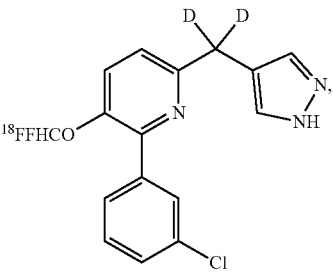
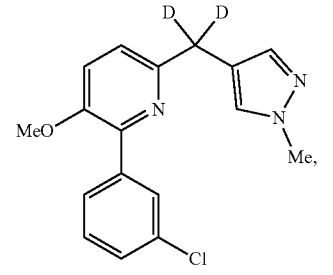
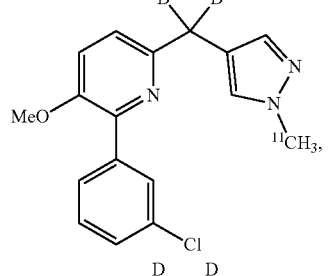
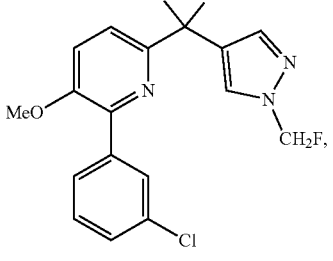
-continued
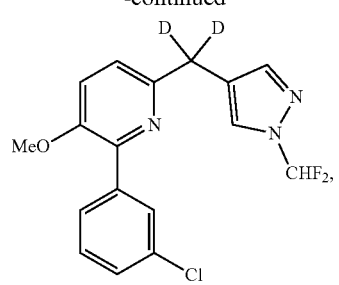
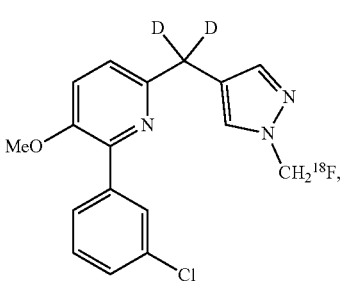
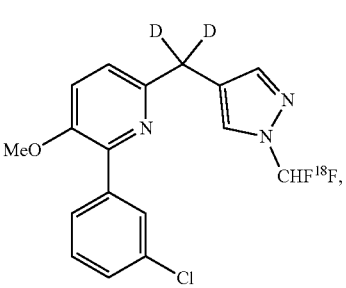
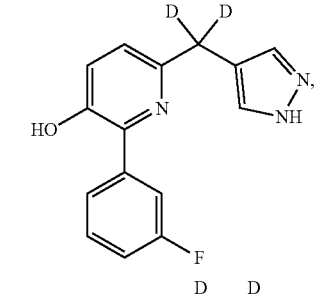
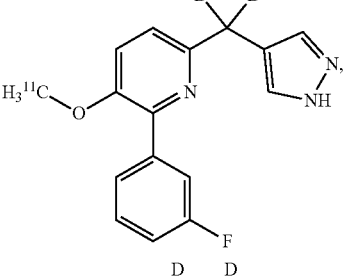
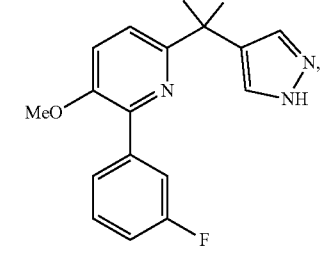

-continued
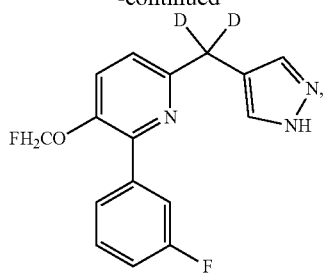
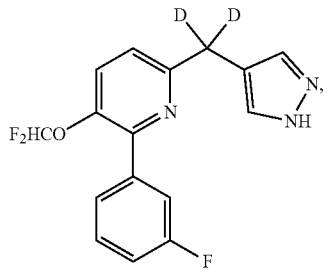
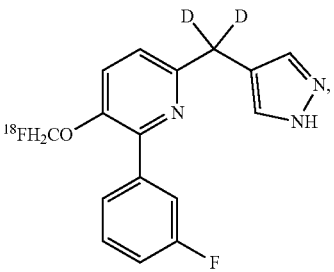
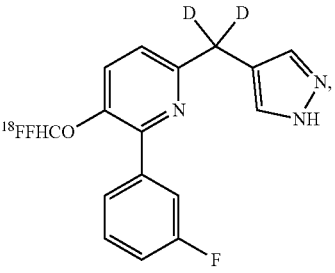
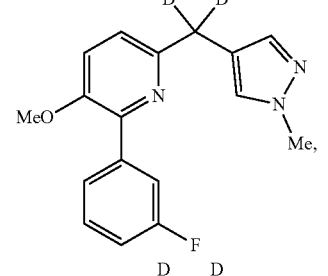
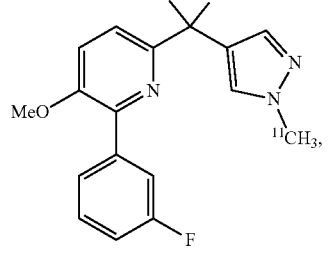
-continued
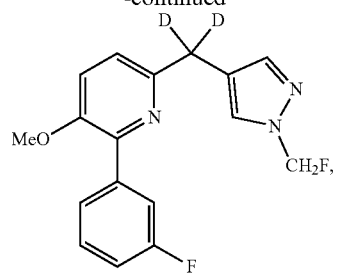
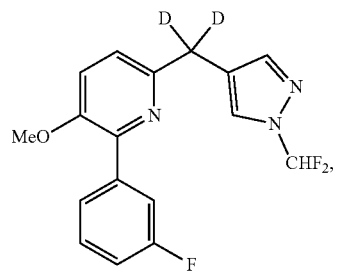
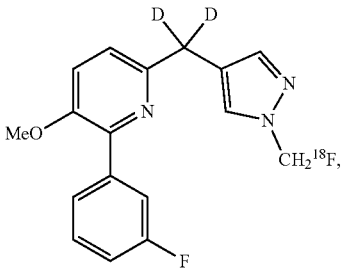
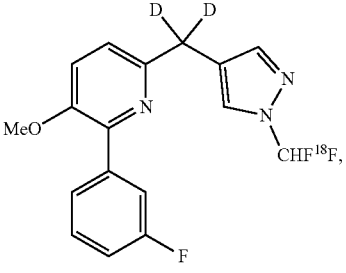
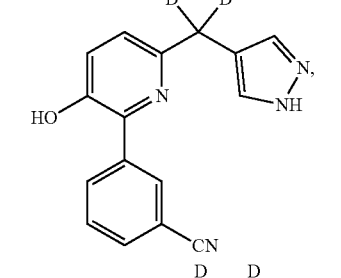
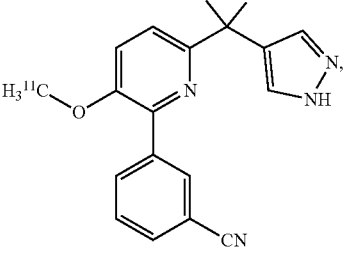

-continued

-continued
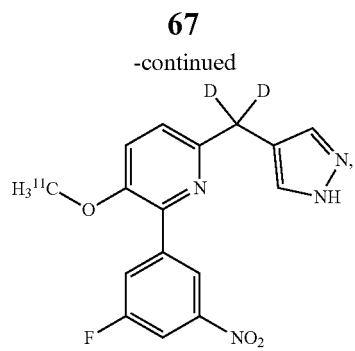
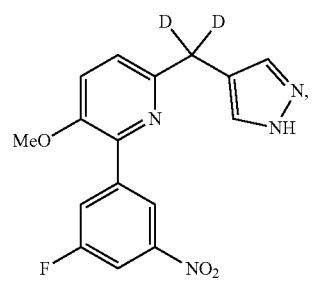
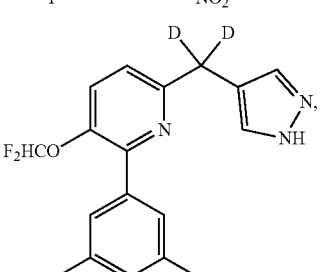
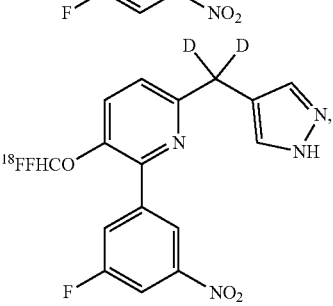
-continued
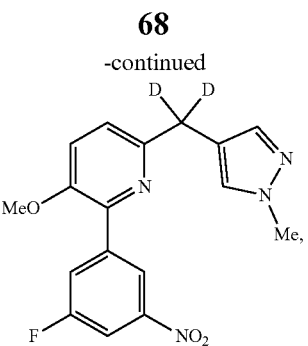
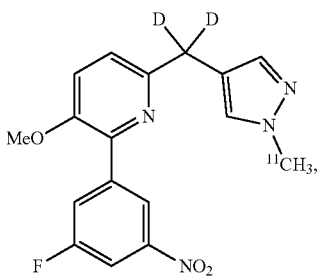
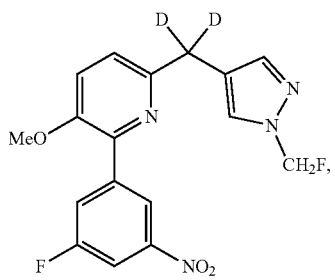
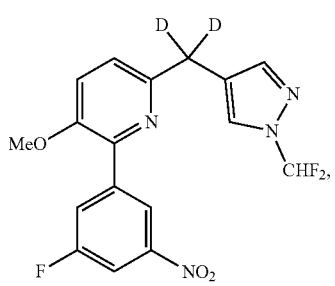
and -continued
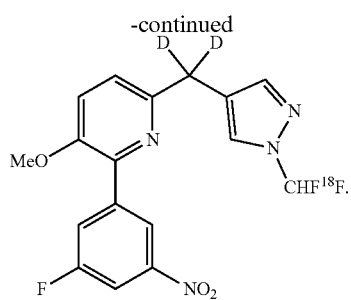
22. The compound of claim 21, having a structure:
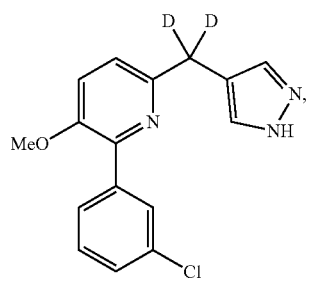
-continued
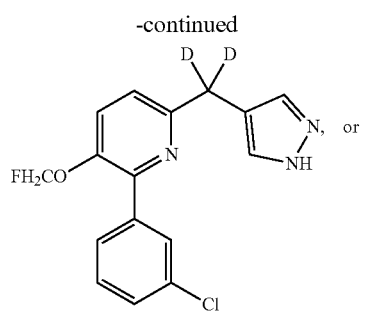
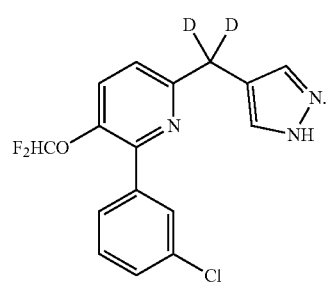
* * * * *